US011241514B2

(12) United States Patent
Mehnert et al.

(10) Patent No.: US 11,241,514 B2
(45) Date of Patent: *Feb. 8, 2022

(54) FORMED THREE-DIMENSIONAL MATRIX AND ASSOCIATED COATING PROVIDING MODULATED RELEASE OF VOLATILE COMPOSITIONS

(71) Applicant: Enviroscent, Inc., Atlanta, GA (US)

(72) Inventors: Eric Mehnert, Lawrenceville, GA (US); Bao Trong Do, Decatur, GA (US); Nicholas D. McKay, Jr., Atlanta, GA (US); Jeffrey S. Sherwood, Ellijay, GA (US)

(73) Assignee: ENVIROSCENT, INC., Atlanta, GA (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/826,428

(22) Filed: Mar. 23, 2020

(65) Prior Publication Data
US 2020/0237949 A1    Jul. 30, 2020

Related U.S. Application Data

(63) Continuation of application No. 15/580,865, filed as application No. PCT/US2016/036672 on Jun. 9, 2016, now Pat. No. 10,596,290.

(Continued)

(51) Int. Cl.
*A61L 9/03* (2006.01)
*C09D 103/02* (2006.01)
(Continued)

(52) U.S. Cl.
CPC ............. *A61L 9/03* (2013.01); *A61L 9/013* (2013.01); *A61L 9/02* (2013.01); *C09D 103/02* (2013.01);
(Continued)

(58) Field of Classification Search
CPC ... A61L 9/013; A61L 9/02; A61L 9/03; C08K 2201/005; C08K 3/36; C09D 103/02; C09J 103/02; C09J 2403/001
See application file for complete search history.

(56) References Cited

U.S. PATENT DOCUMENTS 324,853 A    8/1885 Laurier
855,984 A    6/1907 Russell
(Continued)

FOREIGN PATENT DOCUMENTS

CA    3014426    12/2016
CN    1341357    3/2002
(Continued)

OTHER PUBLICATIONS

"Games Browse Thesaurus Word of the Day Words at Play", Vase, Definition of Vase by Merriam-Webster, Available Online at: https://www.merriam-webster.com/dictionary/vas, Accessed from Internet on: Mar. 24, 2021, pp. 1-11.
(Continued)

*Primary Examiner* — Frances Tischler
(74) *Attorney, Agent, or Firm* — Kilpatrick Townsend & Stockton LLP

(57) ABSTRACT

Described are bonding modulating coatings configured to provide an improved release profile of a volatile composition from a scent reservoir, wherein the modulating coating includes a barrier substance configured to hinder the release of the volatile composition through the modulating coating. The modulating coating also includes a hygroscopic substance that facilitates the release of the volatile composition through the modulating coating. The barrier substance and hygroscopic substance are mixed in a proportion such that the modulating coating provides a bonding action between adjacent scent reservoirs and may be formulated to maintain bonding even under the application of heat. The bonding
(Continued)

modulating coating may then be used to bond a number of scent reservoirs together into a larger, three-dimensional matrix to provide improved scent retention and longevity.

20 Claims, 11 Drawing Sheets

Related U.S. Application Data

(60) Provisional application No. 62/173,264, filed on Jun. 6, 2015.

(51) Int. Cl.
*A61L 9/013* (2006.01)
*A61L 9/02* (2006.01)
*C09J 103/02* (2006.01)
*C08K 3/36* (2006.01)

(52) U.S. Cl.
CPC .............. *C09J 103/02* (2013.01); *C08K 3/36* (2013.01); *C08K 2201/005* (2013.01); *C09J 2403/001* (2013.01)

(56) References Cited

U.S. PATENT DOCUMENTS

| | | |
|---|---|---|
| 934,502 A | 9/1909 | Canon |
| 1,777,820 A | 10/1930 | Anenberg |
| 1,878,401 A | 9/1932 | John |
| 1,988,141 A | 1/1935 | Schaller |
| 2,120,204 A | 6/1938 | Langhorst |
| 2,303,073 A | 11/1942 | Brown |
| 2,615,754 A | 10/1952 | Lindenberg |
| 2,626,833 A | 1/1953 | Valentine |
| 2,800,457 A | 6/1957 | Green et al. |
| 3,041,288 A | 6/1962 | Anthony |
| 3,415,758 A | 12/1968 | Powell et al. |
| 3,516,941 A | 6/1970 | Matson |
| 3,575,345 A | 4/1971 | Buck, Jr. |
| 3,634,564 A | 1/1972 | Okamoto et al. |
| 3,770,856 A | 11/1973 | Ueki et al. |
| 3,790,081 A | 2/1974 | Thornton et al. |
| 3,870,542 A | 3/1975 | Ida et al. |
| 3,954,928 A | 5/1976 | Omori et al. |
| 4,020,156 A | 4/1977 | Murray et al. |
| 4,081,384 A | 3/1978 | Pracht |
| 4,210,487 A | 7/1980 | Driscoll |
| 4,234,627 A | 11/1980 | Schilling |
| 4,384,589 A | 5/1983 | Morris |
| 4,753,389 A | 6/1988 | Davis |
| 4,802,626 A | 2/1989 | Forbes et al. |
| 5,103,654 A | 4/1992 | Gee et al. |
| 5,112,688 A | 5/1992 | Michael |
| 5,145,842 A | 9/1992 | Driedger et al. |
| 5,372,303 A | 12/1994 | Paul |
| 5,395,047 A | 3/1995 | Pendergrass, Jr. |
| 5,437,410 A | 8/1995 | Babasade |
| 5,503,332 A | 4/1996 | Glenn |
| 5,544,812 A | 8/1996 | Torres |
| 5,578,563 A | 11/1996 | Trinh et al. |
| 5,710,406 A | 1/1998 | Garris et al. |
| 5,763,038 A | 6/1998 | Wood |
| 5,763,788 A | 6/1998 | Friedhoff et al. |
| 5,771,503 A | 6/1998 | Valimaa et al. |
| 5,832,648 A | 11/1998 | Malone |
| 5,940,921 A | 8/1999 | Wood et al. |
| 6,014,788 A | 1/2000 | Jaffri |
| 6,039,488 A | 3/2000 | Krawczyk et al. |
| 6,143,675 A | 11/2000 | McCollam et al. |
| 6,158,668 A | 12/2000 | Burgeson |
| 6,168,088 B1 | 1/2001 | Mobley |
| 6,183,596 B1 | 2/2001 | Matsuda et al. |
| 6,194,375 B1 | 2/2001 | Ness et al. |
| D438,606 S | 3/2001 | Jackson |
| D439,318 S | 3/2001 | Jackson |
| D439,644 S | 3/2001 | Jackson |
| 6,214,163 B1 | 4/2001 | Matsuda et al. |
| 6,248,703 B1 | 6/2001 | Finucane et al. |
| 6,261,483 B1 | 7/2001 | Frank et al. |
| 6,329,057 B1 | 12/2001 | Dungworth et al. |
| 6,575,383 B2 | 6/2003 | Dobler et al. |
| 6,668,482 B1 | 12/2003 | Ruffin et al. |
| 6,688,551 B1 | 2/2004 | He et al. |
| 6,803,033 B2 | 10/2004 | McGee et al. |
| 6,921,024 B2 | 7/2005 | Donnelly et al. |
| 6,954,963 B2 | 10/2005 | McKay |
| 7,235,261 B2 | 6/2007 | Smith et al. |
| D605,747 S | 12/2009 | Butler et al. |
| 7,741,266 B2 | 6/2010 | Bell et al. |
| 8,119,064 B2 | 2/2012 | Woo et al. |
| D693,449 S | 11/2013 | Wolf |
| D711,525 S | 8/2014 | Sanders et al. |
| 8,919,662 B2 | 12/2014 | Sherwood |
| D721,168 S | 1/2015 | Wolf |
| 9,132,204 B2 | 9/2015 | McKay et al. |
| 9,149,552 B1 | 10/2015 | Do et al. |
| 9,309,487 B2 | 4/2016 | Denutte et al. |
| 9,381,266 B2 | 7/2016 | Sherwood |
| 9,694,096 B2 | 7/2017 | McKay et al. |
| 9,694,097 B2 | 7/2017 | Do et al. |
| D800,286 S | 10/2017 | McKay et al. |
| 9,795,702 B2 | 10/2017 | Huynh |
| 10,286,098 B2 | 5/2019 | Sherwood |
| 10,596,290 B2 | 3/2020 | Mehnert et al. |
| 10,647,868 B2 | 5/2020 | Do et al. |
| 10,953,125 B2 | 3/2021 | Mehnert et al. |
| 10,987,445 B2 | 4/2021 | McKay et al. |
| 2002/0136886 A1 | 9/2002 | He et al. |
| 2003/0024997 A1 | 2/2003 | Welch et al. |
| 2003/0211799 A1 | 11/2003 | Yao et al. |
| 2004/0001891 A1 | 1/2004 | Smith et al. |
| 2004/0005146 A1 | 1/2004 | Wefler |
| 2005/0204493 A1 | 9/2005 | Legus et al. |
| 2007/0187524 A1 | 8/2007 | Sherwood |
| 2007/0224232 A1 | 9/2007 | Sherwood |
| 2007/0237498 A1 | 10/2007 | Helf et al. |
| 2008/0008860 A1 | 1/2008 | Murray et al. |
| 2008/0009616 A1 | 1/2008 | Frank et al. |
| 2008/0017667 A1 | 1/2008 | Valinotti |
| 2008/0286143 A1 | 11/2008 | Grodsky |
| 2008/0308648 A1 | 12/2008 | Pesu |
| 2011/0148329 A1 | 6/2011 | Demarest et al. |
| 2011/0256364 A1 | 10/2011 | Boyer et al. |
| 2011/0262377 A1 | 10/2011 | McKay et al. |
| 2011/0263477 A1 | 10/2011 | Scarabaggio et al. |
| 2015/0108242 A1 | 4/2015 | Sherwood |
| 2015/0136872 A1 | 5/2015 | Sherwood |
| 2015/0374869 A1 | 12/2015 | McKay et al. |
| 2016/0089468 A1 | 3/2016 | Do et al. |
| 2016/0136317 A9 | 5/2016 | Sherwood |
| 2016/0136318 A9 | 5/2016 | Sherwood |
| 2016/0279276 A1 | 9/2016 | Sherwood |
| 2016/0279277 A1 | 9/2016 | Sherwood |
| 2017/0266333 A1 | 9/2017 | McKay et al. |
| 2017/0296688 A1 | 10/2017 | Do et al. |
| 2018/0133354 A1 | 5/2018 | Mehnert et al. |
| 2018/0326109 A1 | 11/2018 | McKay et al. |
| 2019/0231919 A1 | 8/2019 | Mehnert et al. |
| 2019/0240366 A1 | 8/2019 | Sherwood |
| 2020/0164097 A1 | 5/2020 | Do et al. |
| 2020/0239723 A1 | 7/2020 | Do et al. |

FOREIGN PATENT DOCUMENTS

| | | |
|---|---|---|
| EP | 0462605 | 12/1991 |
| EP | 1190725 | 3/2002 |
| EP | 1627647 | 2/2006 |
| EP | 3307333 | 4/2018 |
| GB | 914421 | 1/1963 |
| GB | 1221488 | 2/1971 |
| GB | 1226448 | 3/1971 |
| GB | 1387265 | 3/1975 |
| JP | 49072551 | 6/1974 |

(56) References Cited

FOREIGN PATENT DOCUMENTS

| | | |
|---|---|---|
| JP | 53159844 | 12/1978 |
| JP | 59154255 | 10/1984 |
| JP | 06284845 | 10/1994 |
| JP | 08289925 | 11/1996 |
| JP | 09276384 | 10/1997 |
| JP | 10273173 | 10/1998 |
| JP | 2000093495 | 4/2000 |
| JP | 2000107274 | 4/2000 |
| JP | 2000312712 | 11/2000 |
| JP | 2001224675 | 8/2001 |
| JP | 2006333904 | 12/2006 |
| JP | 2007051398 | 3/2007 |
| JP | 2008127360 | 6/2008 |
| JP | 2010026976 | 2/2010 |
| JP | 2011057570 | 3/2011 |
| JP | D1431480 | 1/2012 |
| KR | 300645686 | 6/2012 |
| WO | 9112029 | 8/1991 |
| WO | 9807405 | 2/1998 |
| WO | 9842818 | 10/1998 |
| WO | 9844294 | 10/1998 |
| WO | 9847477 | 10/1998 |
| WO | 9847478 | 10/1998 |
| WO | 9943667 | 9/1999 |
| WO | 0072951 | 12/2000 |
| WO | 02089862 | 11/2002 |
| WO | 2004020566 | 3/2004 |
| WO | 2006002395 | 1/2006 |
| WO | 2007016705 | 2/2007 |
| WO | 2006002395 | 8/2007 |
| WO | 2007135424 | 11/2007 |
| WO | 2009078038 | 6/2009 |
| WO | 2010090237 | 8/2010 |
| WO | 2011123723 | 10/2011 |
| WO | 2011129896 | 10/2011 |
| WO | 2013064501 | 5/2013 |
| WO | 2014025720 | 2/2014 |
| WO | 2014181015 | 11/2014 |
| WO | 2016053802 | 4/2016 |
| WO | 2016201089 | 12/2016 |
| WO | 2017124047 | 7/2017 |
| WO | 2018064449 | 4/2018 |

OTHER PUBLICATIONS

U.S. Appl. No. 17/169,185, Articles Formed of Pulp Base Materials With Modulated Scent Release filed Feb. 5, 2021.
International Application No. PCT/US2016/036672, Invitation to Pay Additional Fees and, Where Applicable, Protest Fee, dated Aug. 23, 2016, 7 pages.
U.S. Appl. No. 15/580,865, Non-Final Office Action, dated Aug. 23, 2019, 14 pages.
International Application No. PCT/US2016/036672, International Preliminary Report on Patentability, dated Dec. 21, 2017, 13 pages.
U.S. Appl. No. 15/580,865, Notice of Allowance, dated Nov. 15, 2019, 12 pages.
International Application No. PCT/US2016/036672, International Search Report and Written Opinion, dated Oct. 18, 2016, 21 pages.

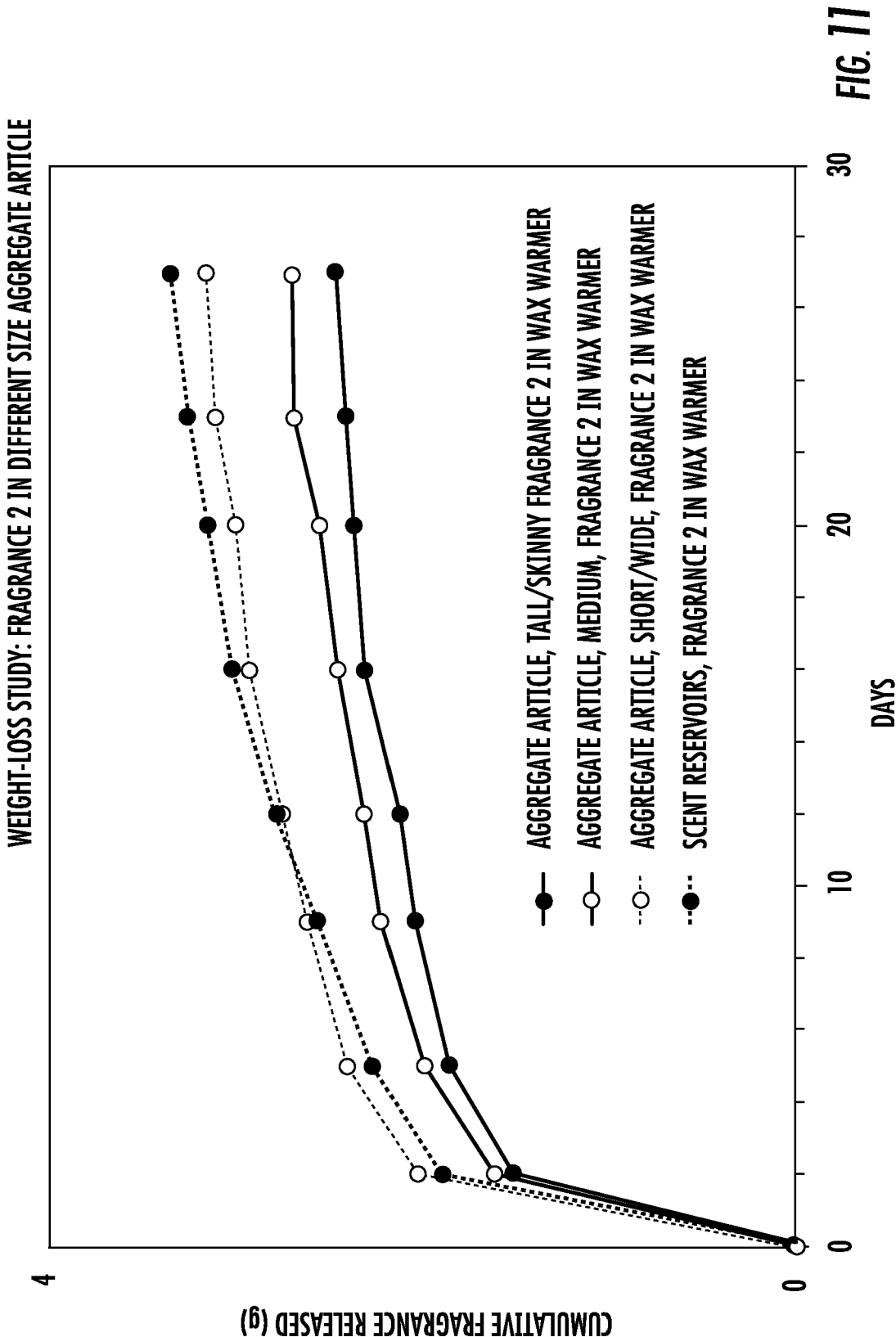

FORMED THREE-DIMENSIONAL MATRIX AND ASSOCIATED COATING PROVIDING MODULATED RELEASE OF VOLATILE COMPOSITIONS

CROSS-REFERENCE TO RELATED APPLICATIONS

This application is a continuation of allowed U.S. patent application Ser. No. 15/580,865, filed Dec. 8, 2017, which is a National Stage Entry of PCT/US2016/036672, filed Jun. 9, 2016, which claims the benefit of U.S. Provisional Application No. 62/173,264, filed Jun. 9, 2015, the entire contents of each of which are incorporated herein by reference.

FIELD OF THE INVENTION

The field of the invention relates to articles that provide modulated release of volatile compositions, and more specifically relate to articles that provide a modulated release of volatile olfactory or fragrance compounds.

BACKGROUND

Fragrance-releasing devices are well known and commonly used in household and commercial establishments to provide a pleasant environment for people in the immediate space. Further, aroma-driven experiences are well recognized to improve or enhance the general mood of individuals. In some instances, fragrances may trigger memories of experiences associated with the specific scent. Whether it is providing a pleasant environment, affecting a general demeanor, or triggering a nostalgic memory, a steady, long-lasting release of fragrance will ensure consumer and customer satisfaction.

Fragrance-release devices based on passive diffusion are limited in their product-use by a finite supply of the fragrance and its evaporation rate from a surface. In some examples, the fragrance-release device is designed to carry the fragrance liquid within its architecture so that the fragrance supply is finite and determined by the size of the fragrance-release device.

The evaporation rate of fragrance from the fragrance-release device is determined, at least in part, by the composition of the fragrance, where compositions containing more volatile compounds (e.g. "top" notes) will evaporate faster than those with less volatile compounds (e.g. "base" notes), and the temperature of the fragrance-release device. A fragrance composition determines its character. As a result, changing the composition of the fragrance may affect the character. The release rate profile of fragrance is generally strong (more intense) at the beginning of product use, followed by decreasing intensity over time. In some instances, the initial fragrance release is too strong and the fragrance release time is too short. For these fragrances, there is a need to modulate the release of fragrance from the fragrance-release device to provide a steady and long-lasting fragrance release without changing the fragrance load and character.

One method of enhancing the transfer of scent from a fragrance-release device into the surrounding environment is to apply heat. Heat may serve to increase the evaporation rate of volatile compounds from a fragrance-release device, especially in the later stages of use when lower levels of fragrance remain. Heating a fragrance-release device may also provide more complete release of fragrance by fully vaporizing any remaining volatile compounds at a rate that is still detectable by a person in the vicinity of the device. However, heating a fragrance-release device may lead to degradation or disintegration of the fragrance-release device. Also, without proper control over the rate of scent release, heating a fragrance-release device may lead to undesirably strong scents or early depletion of the fragrance reservoir.

Specifically there is a need to temper the release of fragrance compounds in heated fragrance-release devices. A fragrance-release device must not only control the release of scent into the surrounding environment, but also resist deterioration and disintegration under thermal stress.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a bonding modulating coating may be configured to provide an improved release profile of a volatile composition from a scent reservoir. The bonding modulating coating comprises a barrier substance configured to hinder a release of the volatile composition through the bonding modulating coating and a hygroscopic substance configured to facilitate the release of the volatile composition through the bonding modulating coating. The barrier substance and the hygroscopic substance may be mixed in proportion to provide bonding between adjacent scent reservoirs.

In certain embodiments, the hygroscopic substance may be configured to facilitate the release of the volatile composition through the bonding modulating coating by attracting water molecules into the bonding modulating coating to displace the volatile composition trapped by the barrier substance within the bonding modulating coating.

In some embodiments, the hygroscopic substance may comprise a silica suspension.

In certain embodiments, the barrier substance may comprise a liquid starch.

In some embodiments, the bonding modulating coating may be configured to resist temperatures higher than ambient. The bonding modulating coating may be configured to resist direct heating.

In certain embodiments, the wet weight ratio of the barrier substance to the hygroscopic substance may be approximately 25:75. The wet ratio of the barrier substance to the hygroscopic substance may also be approximately 25:75:25.

In some embodiments, the bonding modulating coating may comprise approximately 45 to 60 percent barrier substance by wet weight. In further embodiments, the bonding modulating coating may comprise 40 to 55 percent hygroscopic substance by wet weight.

In certain embodiments, a wet weight ratio of the barrier substance to the hygroscopic substance may be approximately 55:45.

In some embodiments, a particle size of the hygroscopic substance may range from 0.001 µm-1 µm.

According to certain embodiments of the present invention, an aggregate article may comprise a plurality of scent reservoirs that may comprise an internal structure, a volatile composition, wherein at least some of the volatile composition may be located in the internal structure, and a modulating coating substantially covering at least one of the plurality of scent reservoirs, wherein the modulating coating comprises a barrier substance and a hygroscopic substance. The modulating coating may be configured to bond the plurality of scent reservoirs into a three-dimensional matrix.

In some embodiments, the hygroscopic substance may comprise a silica suspension. In further embodiments, the barrier substance may comprise a liquid starch.

In certain embodiments, the modulating coating may be configured to resist temperatures higher than ambient. The modulating coating may be configured to resist direct heating.

In some embodiments, a wet weight ratio of the barrier substance to the hygroscopic substance may be approximately 25:75. In further embodiments, a wet weight ratio of the barrier substance to the hygroscopic substance may be 75:25.

In certain embodiments, the modulating coating may comprise approximately 45 to 60 percent barrier substance by wet weight. In further embodiments, the modulating coating may comprise approximately 40 to 55 percent hygroscopic substance by wet weight.

In some embodiments, a wet weight ratio of the barrier substance to the hygroscopic substance may be approximately 55:45.

In certain embodiments, a particle size of the hygroscopic substance may range from 0.001 µm-1 µm.

In some embodiments, the plurality of scent reservoirs may comprise at least one scent reservoir selected from the group consisting of wound paper, extruded pulp, wood chips, fiber bundles, and ceramic chunks.

In certain embodiments, at least some of the volatile composition may be located within the modulating coating, wherein the modulating coating further comprises water that is absorbed or adsorbed to the hygroscopic substance.

According to certain embodiments of the present invention, an aggregate article may comprise a plurality of scent reservoirs that may comprise an internal structure that may comprise pores, a volatile composition, wherein at least some of the volatile composition may be located in the pores, and a modulating coating distributed on exteriors surfaces of the plurality of scent reservoirs. The modulating coating may be formulated to provide a heat resistant bond between the plurality of scent reservoirs, and the modulating coating may regulate the release rate of the volatile composition located in the pores.

According to certain embodiments of the present invention, a method for making an aggregate article may comprise coating a plurality of scent reservoirs with a bonding modulating coating, depositing the plurality of scent reservoirs within a perforated mold, compacting the plurality of scent reservoirs within the perforated mold, drying the plurality of scent reservoirs within the perforated mold, and releasing the plurality of scent reservoirs from the perforated mold.

In some embodiments, the plurality of scent reservoirs may be infused with a volatile composition after coating. In further embodiments, the plurality of scent reservoirs may be dyed prior to coating.

In certain embodiments, the plurality of scent reservoirs may be infused with a volatile composition after releasing the plurality of scent reservoirs from the perforated mold.

In some embodiments, infusing the plurality of scent reservoirs with the volatile composition comprises at least one of adding the volatile composition with a dropper, dipping the plurality of scent reservoirs into the volatile composition, running the plurality of scent reservoirs through a volatile composition curtain, or infusing the volatile composition under a vacuum.

BRIEF DESCRIPTION OF THE DRAWINGS

In the following detailed description, embodiments of the invention are described referring to the following figures:

FIG. 11 is a graph showing a comparison of the cumulative amount released of a fragrance for different geometries of aggregate fragrance-release devices and loose scent reservoirs in a heated condition.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1:
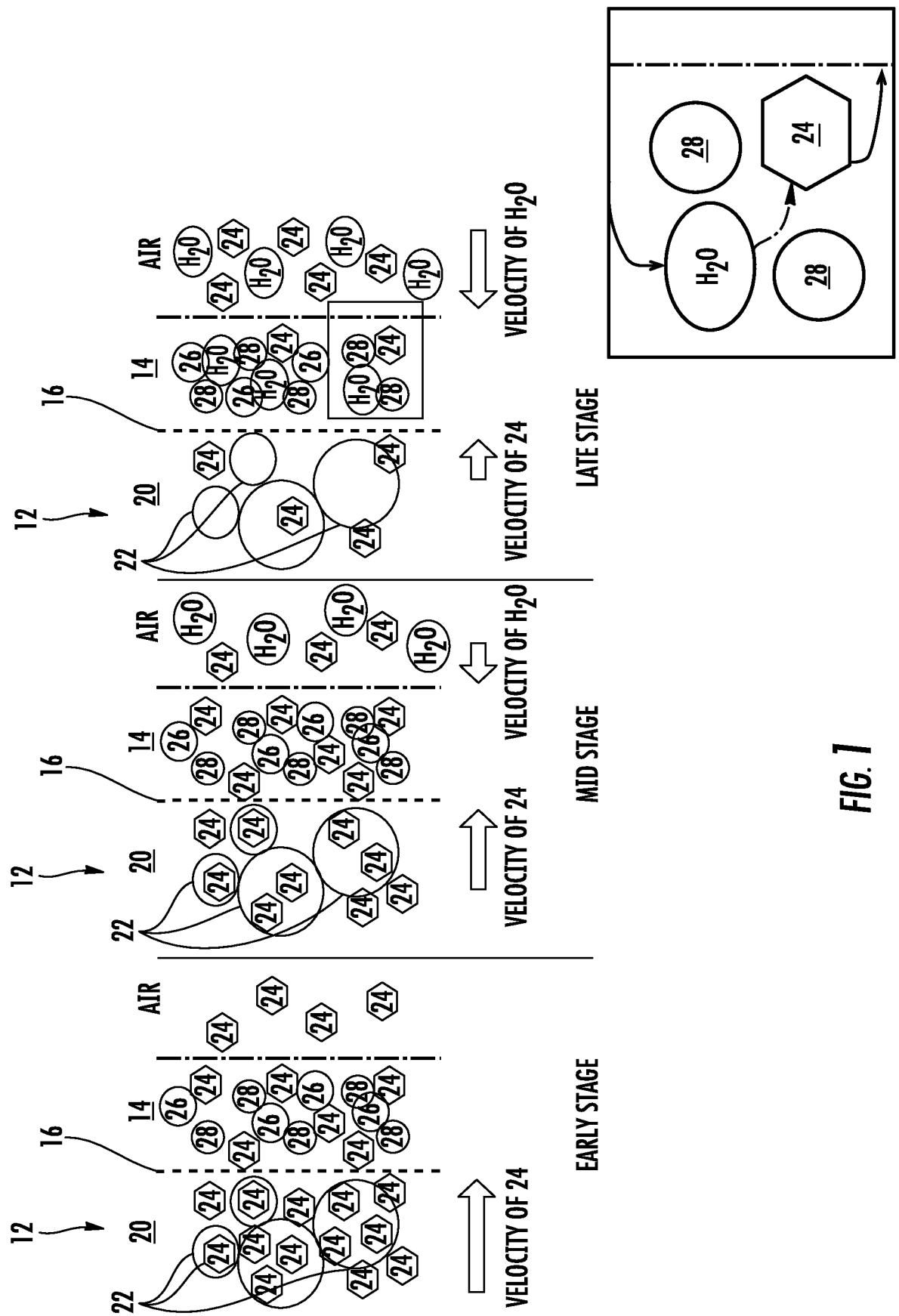
FIG. 1 is a schematic illustrating the movement of a volatile composition across an internal structure of a base material and a modulating coating over time, according to certain embodiments of the present invention.

According to certain embodiments of the present invention shown in FIG. 1, an article comprises a base material 12 and a modulating coating 14. The base material 12 may comprise an internal structure 20 comprising a plurality of pores 22 that are configured to provide locations for the volatile composition 24 to be stored therein and released therefrom, which is described in detail below. The modulating coating 14 may provide a structural function in addition to modulating the release of a fragrance or other volatile compound contained within the pores 22 of the internal structure 20 of the base material 12. For example, the modulating coating 14 may be used to bond a number of individual articles together to form an aggregate structure. In some embodiments, the modulating coating 14 may be specifically formulated to resist the application of heat or higher than ambient temperatures, such as when the article is placed on a warmer.

As used herein, "coating" refers to any composition that can be applied using any suitable method to at least one of an outer surface of a three-dimensional article, to some or all surfaces of a base material 12, and/or may be uniformly or non-uniformly mixed throughout the internal structure 20 of the base material 12 and/or the article. In cases of surface application, the coating may be applied so that the composition may or may not penetrate to at least some degree within the article and/or the base material 12.

The base material 12 may comprise natural and/or synthetic pulp compositions; pulp compositions combined with other products, including but not limited to paper, cellulose, cellulose acetate, pulp lap, cotton linters, biological plant-derived materials (from living plants), synthesized pulp compositions, and mixed pulps; polymer material; porous material; and/or extrudate.

As known in the art, pulp is primarily a collection of fibers with other components of the source material, wherein the fibers are derived from a natural or synthetic source material, for example, biological plants (natural) or petroleum-based synthesis products (synthetic). Pulp may be produced from various types of woods using any one of several known pulping techniques. The pulp may be from hardwoods, softwoods, or mixtures thereof. The pulp may also be made from recycled materials, and comprises recovering waste paper and remaking it into new products.

In certain embodiments, the number and/or size of the plurality of pores 22 (i.e., porosity) within the base material 12 may be controlled by the compactness and/or size of the fibers and/or particles that form the internal structure 20. For example, in certain embodiments of the base material 12 that comprise fibers, voids between the fibers form tiny air passages throughout the internal structure 20. The compactness of the fibers affects the degree in which the base material 12 allows gas or liquid to pass through it. For example, porosity may affect uptake or load amount of volatile compositions, or may affect the rate of release of such substances. Porosity of the base material 12 may be affected by adding other materials, such as additives to the base material 12 as it is being formed from a composition, such as pulp or any other composition described above, so that the additives are located within the internal structure 20 of the base material 12 after formation.

The porosity of a base material 12 that comprises pulp may be affected at any stage of the pulp production process. An increased level of fiber refining causes the fibers to bond together more strongly and tightly, making the pulp material denser, thereby reducing the network of air passages and the porosity. Surface sizing, coating, calendering or supercalendering may also seal and/or further compress surface fibers.

The porosity of the base material 12 is measured quantitatively as either the length of time it takes for a quantity of air to pass through a sample, or the rate of the passage of air through a sample, using either a Gurley densometer (in the first case) or a Sheffield porosimeter (in the second case). With the Gurley densometer, the porosity is measured as the number of seconds required for 100 cubic centimeters of air to pass through 1.0 square inch of a given material at a pressure differential of 4.88 inches of water, as described in ISO 5646-5, TAPPI T-460, or TAPPI T-536.

The porosity may affect how completely and how quickly the volatile composition 24 is absorbed into a pulp base material 12, as such absorption may occur primarily by capillary action. For example, a pulp base material 12 with high porosity may have increased absorbency of the volatile composition 24. The porosity of the pulp base material 12 may range from 0.01 Gurley second-100 Gurley seconds, and all ranges therein. In certain embodiments where there are multiple layers of pulp base material 12, the porosity may range from 0.01 Gurley second-20 Gurley seconds. The volatile composition 24 may be applied to the base material 12 in the form of a film, or a coating, or a treatment integrated into the internal structure 20 of the base material 12.

The volatile composition 24 may include but is not limited to fragrances, flavor compounds, odor-eliminating compounds, aromatherapy compounds, natural oils, water-based scents, odor neutralizing compounds, and outdoor products (e.g., insect repellent).

As used herein, "volatile substance" refers to any compound, mixture, or suspension of compounds that are odorous, or compound, mixture, or suspension of compounds that cancel or neutralize odorous compounds, such as any compound or combination of compounds that would produce a positive or negative olfactory sense response in a living being that is capable of responding to olfactory compounds, or that reduces or eliminates such olfactory responses.

A volatile composition as used herein comprises one or more volatile substances and is generally a composition that has a smell or odor, which may be volatile, which may be transported to the olfactory system of a human or animal, and is generally provided in a sufficiently high concentration so that it will interact with one or more olfactory receptors.

A fragrance may comprise an aroma or odorous compound, mixture or suspension of compounds that is capable of producing an olfactory response in a living being capable of responding to olfactory compounds, and may be referred to herein as odorant, aroma, scent, or fragrance. A fragrance composition may include one or more than one of the fragrance characteristics, including top notes, mid notes or heart, and the dry down or base notes. The volatile composition 24 may comprise other diluents or additives, such as solvents or preservatives.

Examples of volatile compositions 24 useful in the present invention include but are not limited to, esters, terpenes, cyclic terpenes, phenolics, which are also referred to as aromatics, amines and alcohols. For example, furaneol 1-hexanol, cis-3-Hexen-1-ol, menthol, acetaldehyde, hexanal, cis-3-hexenal, furfural, fructone, hexyl acetate, ethyl methylphenylglycidate, dihydrojasmone, wine lactone, oct-1-en-3-one, 2-Acetyl-1-pyrroline, 6-acetyl-2,3,4,5-tetrahydropyridine, gamma-decalactone, gamma-nonalactone, delta-octalactone, jasmine, massoia lactone, sotolon ethanethiol, grapefruit mercaptan, methanethiol, 2-methyl-2-propanethiol, methylphosphine, dimethylphosphine, methyl formate, nerolin tetrahydrothiophene, 2,4,6-trichloroanisole, substituted pyrazines, methyl acetate, methyl butyrate, methyl butanoate, ethyl acetate, ethyl butyrate, ethyl butanoate, isoamyl acetate, pentyl butyrate, pentyl butanoate, pentyl pentanoate, isoamyl acetate, octyl acetate, myrcene, geraniol, nerol, citral, lemonal, geranial, neral, citronellal, citronellol, linalool, nerolidol, limonene, camphor, terpineol, alpha-ionone, terpineol, thujone, benzaldehyde, eugenol, cinnamaldehyde, ethyl maltol, vanillin, anisole, anethole, estragole, thymoltrimethylamine, putrescine, diaminobutane, cadaverine, pyridine, indole and skatole. Most of these are organic compounds and are readily soluble in organic solvents, such as alcohols or oils. Fragrance includes pure fragrances such as those including essential oils and are known to those skilled in the art. Water-based odorous compounds and other odorous compositions are also contemplated by the present invention.

Fragrance oils as olfactory-active compounds or compositions usually comprise many different perfume raw materials. Each perfume raw material used differs from another by several important properties including individual character and volatility. By bearing in mind these different properties, and others, the perfume raw material can be blended to develop a fragrance oil with an overall specific character profile. To date, characters are designed to alter and develop with time as the different perfume raw materials evaporate from the substrate and are detected by the user. For example, perfume raw materials that have a high volatility and low substantivity are commonly used to give an initial burst of characters such as light, fresh, fruity, citrus, green or delicate floral to the fragrance oil, which are detected soon after application. Such materials are commonly referred to in the field of fragrances as "top notes." By way of a contrast, the less volatile, and more substantive, perfume raw materials are typically used to give characters such as musk, sweet, balsamic, spicy, woody or heavy floral to the fragrance oil which, although may also be detected soon after application, also last far longer. These materials are commonly referred to as "middle notes" or "base notes." Highly skilled perfumers are usually employed to carefully blend perfume raw materials so that the resultant fragrance oils have the desired overall fragrance character profile. The desired overall character is dependent both upon the type of composition in which the fragrance oil will finally be used and also the consumer preference for a fragrance.

In addition to the volatility, another important characteristic of a perfume raw material is its olfactory detection level, otherwise known as the odor detection threshold (ODT). If a perfume raw material has a low odor detection threshold, only very low levels are required in the gas phase, or air, for it to be detected by the human, sometimes as low as a few parts per billion. Conversely, if a perfume raw material has a high ODT, larger amounts or higher concentrations in the air of that material are required before it can be smelled by the user. The impact of a material is its function of its gas phase or air concentration and its ODT. Thus, volatile materials, capable of delivering large gas-phase concentrations, which also have low ODTs, are considered to be impactful. To date, when developing a fragrance oil, it has been important to balance the fragrance with both low and high volatility raw materials since the use of too many high volatility materials could lead to a short lived, overwhelming scent. As such the levels of high odor impact perfume raw materials within a fragrance oil have traditionally been restricted.

As used herein the term "fragrance oil" relates to a perfume raw material, or mixture of perfume raw materials, that are used to impart an overall pleasant odor profile to a composition, preferably a cosmetic composition. As used herein the term "perfume raw material" relates to any chemical compound that is odorous when in an un-entrapped state, for example in the case of pro-perfumes, the perfume component is considered to be a perfume raw material, and the pro-chemistry anchor is considered to be the entrapment material. In addition "perfume raw materials" are defined by materials with a C log P value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP," which is available from Daylight Chemical Information Systems Inc., Irvine Calif., USA. Octanol/water partition coefficients are described in more detail in U.S. Pat. No. 5,578,563.

Examples of residual "middle and base note" perfume raw materials include, but are not limited to, ethyl methyl phenyl glycidate, ethyl vanillin, heliotropin, indol, methyl anthranilate, vanillin, amyl salicylate, coumarin. Further examples of residual perfume raw materials include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxylphenyl butanone, 8-cyclohexadecen-1-one, oxocyclohexadecen-2-one/habanolide, florhydral, intreleven aldehyde.

Examples of volatile "top note" perfume raw materials include, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, c is 1,3-oxathiane-2-methyl-4-propyl.

Other useful residual "middle and base note" perfume raw materials include, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Other volatile "top note" perfume raw materials include, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thuj one, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

In certain embodiments, the volatile composition 24 may comprise a fragrance component having a release rate ranging from 0.001 g/day to 2.0 g/day. The formulation of the fragrance may comprise any suitable combination of top, mid, and base note components.

The modulating coating 14 may be applied to at least one outer surface 16 of the base material 12 and/or to the article, and may be applied before or after loading of the volatile composition 24. In certain embodiments, the modulating coating 14 may penetrate into the internal structure 20 of the base material 12 to a certain level, which may vary depending on the porosity, processing methods, or other characteristics of the base material 12. In some embodiments, the modulating coating 14 forms a continuous phase of the barrier substance 26 and the hygroscopic substance 28 dispersed therein when applied to at least one outer surface 16 of the base material 12 and/or the article.

The modulating coating 14 is designed to slow the release rate of the volatile composition 24 loaded into the internal structure 20 at higher concentration levels and accelerate the release rate of the volatile composition 24 at lower concentration levels in order to achieve a relatively steady release of volatile composition 24 over time. The modulating coating 14 also serves to bind smaller, individual scent reservoirs (not shown) into a larger, three-dimensional matrix. In certain embodiments, the modulating coating 14 may be specially formulated to resist the application of heat or high temperatures. The article and modulating coating 14 may then be used with heat to improve the distribution and effectiveness of the fragrance.

To explain the way that the modulating coating 14 works to have this "hold/push" effect over a range of load levels of the volatile composition 24, it is necessary to explain the way in which the release rate of the volatile composition 24 is generated. The volatile composition 24 is loaded or absorbed into the internal structure 20 via the pores 22 until a sufficiently high load level is achieved within the internal structure 20 through various embodiments of loading methods, which are explained in detail below. The volatile composition 24 may be loaded or absorbed into the internal structure 20 before or after the modulating coating 14 is applied.

The initially high load level of the volatile composition 24 within the internal structure 20 creates an internal force that causes the volatile composition 24 to diffuse or evaporate out of the internal structure 20 as quickly as possible to a region of lower concentration. As the load level of the volatile composition 24 decreases over time, the force that causes the diffusion or evaporation diminishes until there is no longer a force remaining (i.e., an equilibrium point is reached where the volatile composition 24 no longer diffuses or evaporates out of the internal structure 20). The equilibrium point is usually higher than 0% concentration, which causes some of the volatile composition 24 to become trapped within the pores 22 of the internal structure 20.

In conventional applications, such as in U.S. Publication No. 20110262377, a coating may be applied to form a layer that slows or retards the rapid release of a volatile composition at higher concentration levels. These conventional coatings typically include substances that trap some of the volatile composition within the coating layer, which slows down the rate of release through the coating. However, because the coating only serves as a barrier or "speed bump" to slow down the rate of release of the volatile composition, the release will eventually stop once the concentration of volatile composition within the internal structure reaches equilibrium (i.e., a level where there is no longer a sufficient concentration to drive the volatile composition through the coating layer, thus allowing some of volatile composition to remain trapped within the coating layer and/or within the internal structure).

The modulating coating 14 comprises both a barrier substance 26 and a hygroscopic substance 28. In particular, in most embodiments, the modulating coating 14 comprises substances that do not chemically interact with the volatile composition 24 itself. Moreover, in certain embodiments, the formulation of the modulating coating 14 is free of any fibrous materials, such as a pulp composition.

In these embodiments, when the modulating coating 14 is applied to the outer surface 16 of the internal structure 20, at the higher concentration levels of the volatile composition 24 within the internal structure 20, the barrier substance 26 forms a barrier or "speed bump" to slow down the rate of release of the volatile composition 24 through the modulating coating 14. At these higher initial concentration levels, as illustrated in the early stage section of FIG. 1, the hygroscopic substance 28 does not play a role in modulating the release rate of the volatile composition 24 (i.e., does not absorb any water into the modulating coating 14) because the concentration of the volatile composition 24 within the internal structure 20 is sufficiently high to force a certain amount of the volatile composition 24 to release through the modulating coating 14 at a rate that effectively blocks any water from being attracted into the modulating coating 14 by the hygroscopic substance 28.

As the concentration level of the volatile composition 24 within the internal structure 20 slowly diminishes, as illustrated in the mid stage section of FIG. 1, the concentration of the volatile composition 24 within the internal structure 20 is still sufficiently high to continue to force some of the volatile composition 24 out of the modulating coating 14 at a reduced rate of release.

One hypothesis to explain the phenomenon observed in the late stage is that because there is a lower volume of the volatile composition 24 exiting the modulating coating 14, the hygroscopic substance 28 begins to attract more water (typically in the form of water vapor) into the modulating coating 14, whereupon the water adsorbs or absorbs to the hygroscopic substance 28 and begins to displace the volatile composition 24 that is trapped by the barrier substance 26 within the modulating coating 14. This hypothesis is illustrated in the late stage section of FIG. 1, and is based on known physical properties of the hygroscopic substance 28 and the data showing higher release rates at the end of the product life cycle, as compared to the same product without the modulating coating 14. Once displaced, the volatile composition 24 is released from the modulating coating 14, thereby creating an aggregate rate of release of the volatile composition 24 that may approximate the rate of release driven by the higher load level of the volatile composition 24 alone.

As the load level of volatile composition 24 continues to drop to a level that can no longer drive the volatile composition 24 out of the modulating coating 14, the hygroscopic substance 28 continues to pull more and more water into the modulating coating 14. That water continues to displace the trapped volatile composition 24, effectively forcing the displaced volatile composition 24 to be released from the modulating coating 14. For a period of time in the late stage, the rate of release of the volatile composition 24 due to water displacement driven by the hygroscopic substance 28 may approximate the rate of release driven by the higher load level of the volatile composition 24 alone and/or may approximate the aggregate rate of release driven by both the higher load level of the volatile composition 24 and water displacement driven by the hygroscopic substance 28. As a result, where conventional coatings that contain only barrier substances 26 may have stopped releasing volatile compositions once the equilibrium point of the concentration is reached within the internal structure 20, the modulating coating 14 continues to provide a relatively constant release of the volatile composition 24.

An alternate hypothesis to explain the phenomenon observed in the late stage is that the water that is brought into the modulating coating 14 by the hygroscopic substance 28 may act to degrade the barrier substance 26, which would also allow for release of the volatile composition 24 trapped within the modulating coating 14 and within the internal structure 20 of the base material 12.

In any event, the test results demonstrate that the modulating coating 14 generates an improved release profile of the volatile composition 24 over the aromatic life cycle of the article, depending on the porosity of the internal structure 20 of the base material 12 and the volatility levels of the volatile composition 24. Eventually, the concentration of the volatile composition 24 within the internal structure 20 and the amount trapped by the barrier substances 26 within the modulating coating 14 will reach such a low point that the amount of volatile composition 24 released on a daily basis by the modulating coating 14 will eventually decline to zero.

In certain embodiments, the barrier substance 26 may comprise liquid starch. In other embodiments, the barrier substance 26 may include but is not limited to maltodextrin (e.g. Maltrin), other dextrins, other film-forming polysaccharides, other carbohydrates (mono-, di-, tri-, etc.), natural unmodified starch, modified starch, any starch appropriate for use in papermaking, as well as combinations of starch types, dextrin types, and combinations of starches and dextrins. In certain embodiments, the barrier substance 26 may include but not is limited to additives such as insolubilizers, lubricants, dispersants, defoamers, crosslinkers, binders, surfactants, leveling agents, wetting agents, surface additives, rheology modifiers, non-stick agents, and other coating additives. In some embodiments, the starch may be liquid, pre-gelled, or a dry modified starch.

In certain embodiments, the hygroscopic substance 28 may comprise silica (e.g. silica nanoparticles) or a silica suspension. In other embodiments, the hygroscopic substance 28 may include but is not limited to other hygroscopic reagents, activated charcoal, calcium sulfate, calcium chloride, and molecular sieves, or other suitable water absorbing materials.

The weight ratio of the barrier substance 26 to the hygroscopic substance 28 may range from 99:1 to 1:99, and all ranges therein between. In certain embodiments, the weight ratio of the barrier substance 26 to the hygroscopic substance 28 may further range from 25:75 to 75:25 wet weight ratio. In yet other embodiments, the weight ratio of the barrier substance 26 to the hygroscopic substance 28 may be approximately 50:50. In certain embodiments, the modulating coating 14 may be formulated specifically for bonding and heat resistance. For example, the modulating coating 14 may be mixed with a wet weight ratio of approximately 45%-60% barrier substance 26 (e.g. liquid modified starch) and approximately 40%-55% hygroscopic substance 28 (e.g. a silica suspension). In some embodiments, the modulating coating 14 may be mixed with a ratio of 55% barrier substance 26 (e.g. liquid modified starch) and 45% hygroscopic substance 28 (e.g. a silica suspension) on a weight basis. However, the ratio of the barrier substance 26 to the hygroscopic substance 28 is adjustable depending on the required adhesive strength and temperature resistance of a particular application. Generally, increasing the proportion of the barrier substance 26 (e.g. liquid modified starch) will improve adhesion. Increases to the hygroscopic substance 28 (e.g. a silica suspension) will tend to increase thermal stability and heat resistance of the modulating coating 14. Changes to the composition of the barrier substance 26 or hygroscopic substance 28 may also influence the properties of the modulating coating 14. For example, using a higher molecular weight compound in the barrier substance 26, as with replacing a liquid modified starch with an un-modified starch, may yield stronger adhesion properties, even with lower concentrations of solids in the barrier substance 26.

In certain embodiments, the particle size of the hygroscopic substance 28 is determined in part by the amount of surface area needed to attract enough water to counteract the drop in release rate due to a reduction in the load level of the volatile composition 24. The hygroscopic substance 28 is also configured so that it will attract water vapor, rather than liquid water. As a result, the diameter of the particle size of the hygroscopic substance 28 may range from 0.001 μm-1 μm, and all ranges therein between, and may further range from 1 nm-100 nm, which will attract the appropriate amount of water vapor molecules, as well as providing a more even coating.

In certain embodiments, the hygroscopic substance 28 may have a surface charge range that ensures interaction with the barrier substances 26. For example, in the case of silica, the surface charge ranges from −10 mV to −4000 mV, as measured by Zeta potential, which is a highly anionic point charge. When the silica is mixed with the liquid starch before coating, the liquid starch may group around the silica particles, which may further assist with the barrier formation within the modulating coating 14.

In certain embodiments, the modulating coating 14 may provide a more consistent release rate of the volatile composition 24. The consistency (variance) may be measured by the following formula.

$$\text{Variance}_{(Weight\text{-}loss\ ratio)} = \text{First day weight-loss value}/\text{Last day weight-loss value}$$

The benefit of the modulating coating 14 is to reduce the variance within a ratio range of 1 to 20 over a life cycle of the article, which in certain embodiments may be 30 days, but could be longer or shorter as needed or desired.

Furthermore, in certain embodiments, use of a more concentrated version of the volatile composition 24 in combination with the modulating coating 14 provides release rate improvement as disclosed herein and presents commercial advantages over the use of the standard version of volatile composition 24 without modulating coating 14. The term "concentrated" used herein is intended to describe a higher amount of olfactory-active compounds or compositions relative to other non-volatile substances within the volatile composition 24. A more concentrated version of a volatile composition 24 will release into the atmosphere faster than its standard version, thus providing a higher than desired scent intensity and character. Application of modulating coating 14 will moderate this faster release, resulting in a new release rate that has the desired intensity and character. A similar performance improvement may be seen with the application of heat to the article 10 or scent reservoirs 11. The application of heat will increase the volatility of the volatile composition 24 relative to room temperature. This increase in volatility will lead to an increase in vapor pressure, and an increase in release rate. The modulating coating 14 can then be formulated to moderate the release rate of the volatile composition 24 to maintain a long-lasting scent release and prevent disintegration of any aggregated scent reservoirs 11 or base materials 12 that may be bonded together by the modulating coating 14. In some embodiments, the modulating coating 14 may be able to withstand constant temperatures of up to one hundred twenty degrees Centigrade.

In certain embodiments, the loaded amount of a more concentrated version of the volatile composition 24 into base material 12 coated with modulating coating 14 may be less than the loaded amount of the standard version of a volatile composition 24. This increased concentration, in combination with the optimal release rate, provides the opportunity for an increased duration of release and/or for material cost savings (by reducing the initial volatile composition load).

The base material 12 may be converted into an article, which may occur before or after the modulating coating 14 and/or the volatile composition 24 are applied.

Figures 2, 2A:
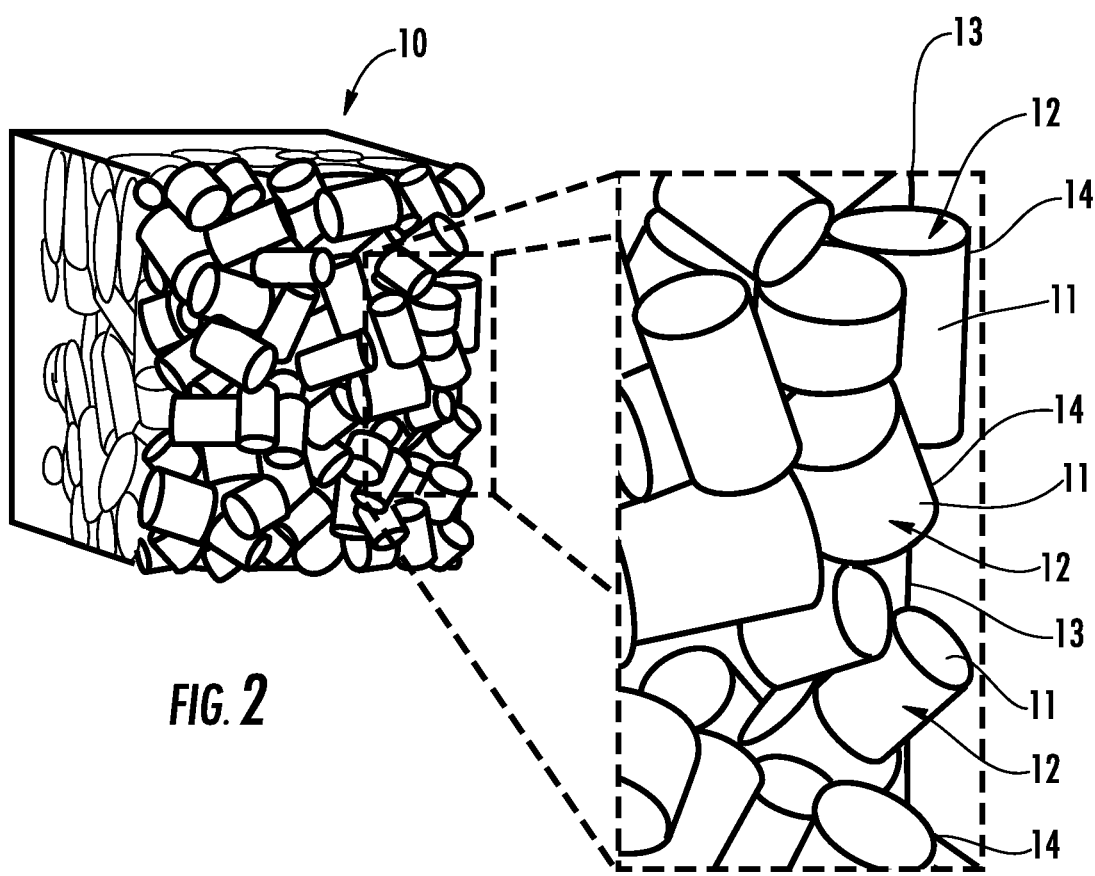
FIG. 2 is a cross-sectional view of an article formed from a plurality of scent reservoirs compacted into an aggregate fragrance-release device, according to certain embodiments of the present invention.
FIG. 2A is an enlarged view of the matrix composition of the fragrance-release device of FIG. 2.
Figure 3:
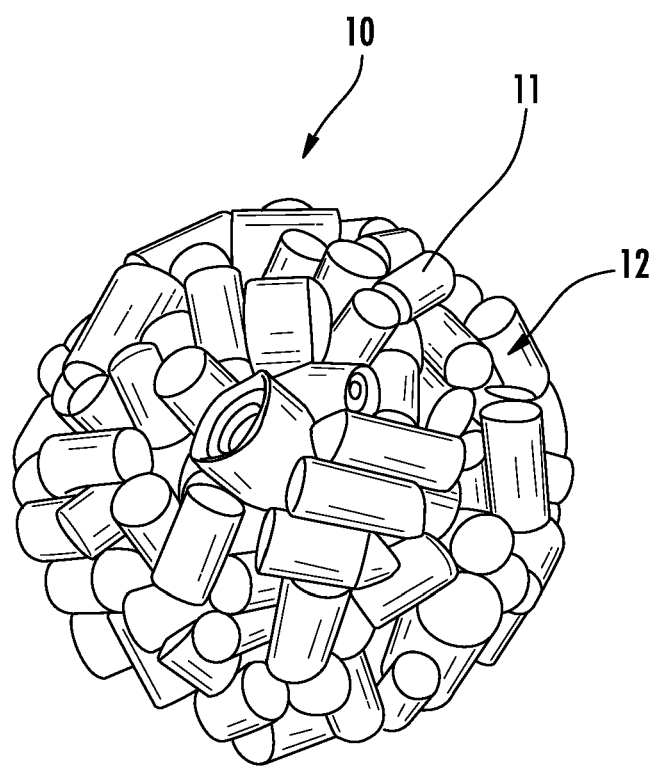
FIG. 3 is a perspective view of a spherical aggregate fragrance-release device.
Figure 4:
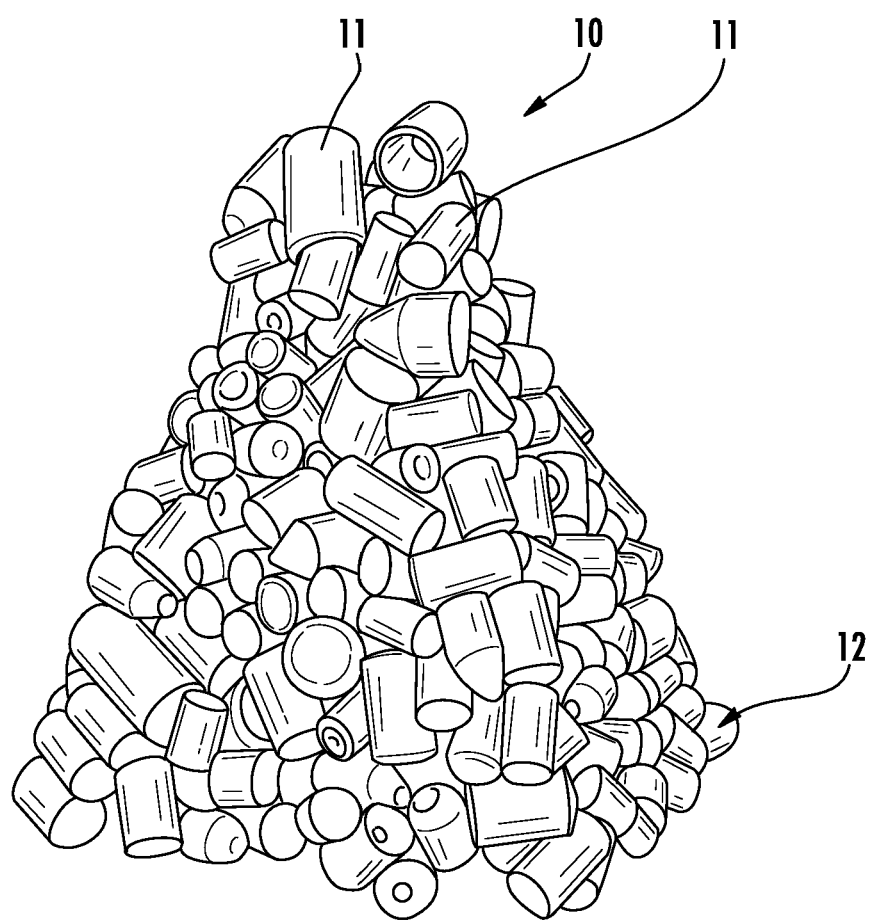
FIG. 4 is a perspective view of a pyramidal aggregate fragrance-release device.
Figure 5:
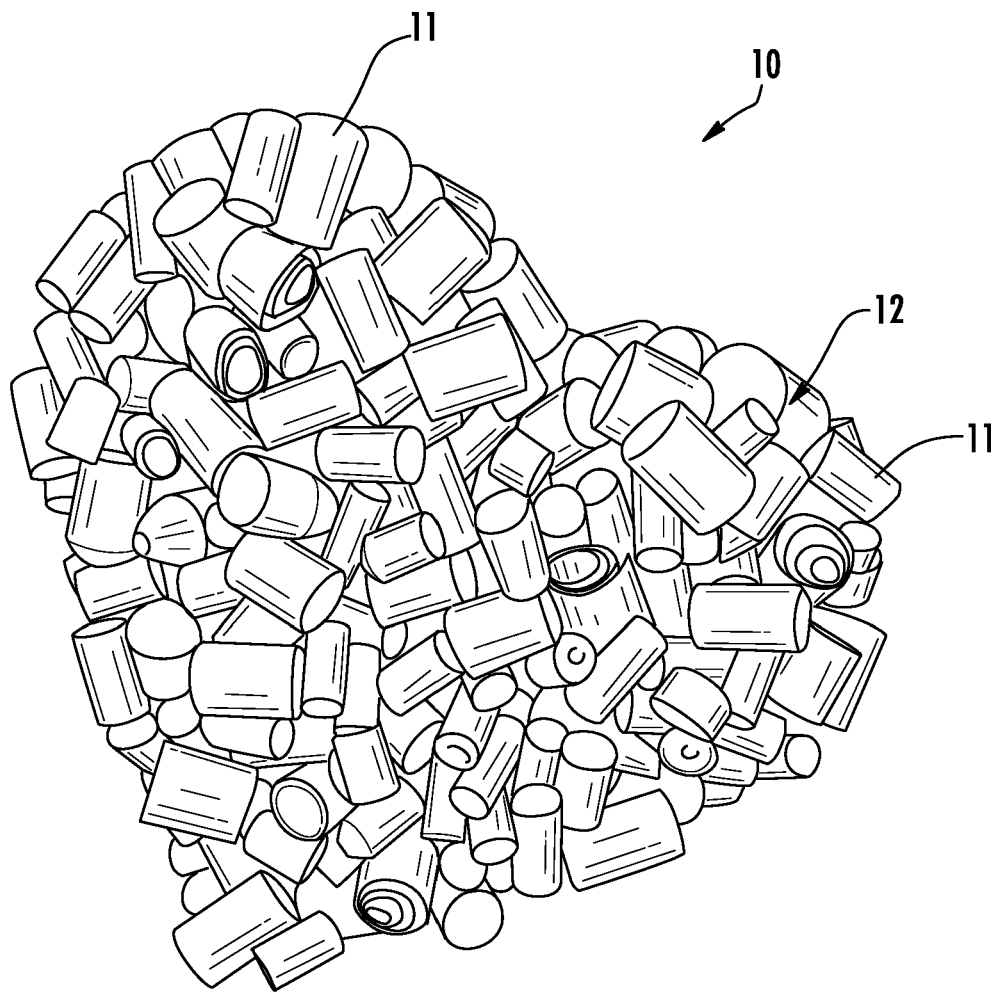
FIG. 5 is a perspective view of a heart-shaped aggregate fragrance-release device.

FIG. 2 is a cross sectional view of an article 10 formed from a plurality of scent reservoirs 11 aggregated and bonded together with a modulating coating 14. The scent reservoirs 11 are comprised of a base material 12 that may be infused with a volatile composition 24 (not shown) either before or after the application of the modulating coating 14. In certain embodiments, the scent reservoirs 11 may be comprised of the trimmings of larger pieces that are to be sold as individual fragrance-release devices. For example, in some embodiments, the scent reservoirs 11 may be the end trimmings of tightly wound paper sticks, which are to be processed and sold separately. In other embodiments, the scent reservoirs 11 may be any type of absorbent or porous material that may be infused with a volatile composition 24 including, but not limited to, wood chips, extruded pulp, fiber bundles, and/or ceramic chunks. Any size of scent reservoir 11 may be bonded together to make an aggregate article 10.

The scent reservoirs 11 may be formed into an aggregate article 10 by bonding them to one another with the modulating coating 14. In some embodiments, the modulating coating 14 may be specifically formulated for a particular purpose. Typically, as noted above, the bonding modulating coating 14 will be comprised of a mixture of a barrier substance 26 and a hygroscopic substance 28. In some cases, it may be desirable to formulate the modulating coating 14 so as to resist heat or high temperatures to allow the aggregate article 10 to be used with a warmer to improve the release and distribution of the fragrance from the base material 12. For example, the modulating coating 14 may be mixed with a ratio of 55% barrier substance 26 (e.g. liquid modified starch) and 45% hygroscopic substance 28 (e.g. a silica suspension) on a weight basis. However, the ratio of the barrier substance 26 to the hygroscopic substance 28 is adjustable depending on the required adhesive strength and temperature resistance of a particular application.

To manufacture an aggregate article 10 from a plurality of scent reservoirs 11, a desired number of scent reservoirs 11 are mixed with the adhesive modulating coating 14. In some embodiments, the ratio of scent reservoirs 11 to modulating coating 14 may be three to one on a weight basis. Said differently and by way of example, the mixture of scent reservoirs 11 and modulating coating 14 may be comprised of 75% scent reservoirs 11 and 25% modulating coating 14 by weight. The ratio of scent reservoirs 11 to modulating coating 14 may be adjusted as necessary for any particular application, but generally may fall within the range of 90% scent reservoirs 11 to 10% modulating coating 14 and 10% scent reservoirs 11 to 90% modulating coating 14 based on weight. The particular ratio of scent reservoirs 11 to modulating coating 14 may be based on, among other things, the shape, size, and/or packing factor of the scent reservoirs 11, and/or the strength, permeability, and/or heat tolerance of the modulating coating 14. In certain embodiments, it may be preferable to infuse the scent reservoirs 11 with a volatile composition 24 and/or coloring agent prior to production of the aggregate article 10. However, it is also possible to infuse the aggregate article 10 with color and fragrance after the production of the aggregate article 10 has been completed. For instance, in certain embodiments, the fragrance may be added to an aggregate article 10 with a dropper, by dipping the aggregate article 10, passing it through a fragrance curtain, infusing fragrance under vacuum, or any other suitable method for infusing or introducing a fragrance or volatile composition 24 into the aggregate article 10.

After the mixture of scent reservoirs 11 and modulating coating 14 has been prepared and well mixed to ensure even and complete coating of the scent reservoirs 11, the mixture may be deposited in a mold that defines the desired end shape of the aggregate article 10. The mixture of scent reservoirs 11 and modulating coating 14 may be pressed or compacted into the mold to ensure complete filling and proper packing of the scent reservoir 11 and modulating coating 14 mixture. As used herein, compaction of the scent reservoir 11 and modulating coating 14 mixture does not necessarily require or involve the distortion or deformation of the scent reservoirs 11. Rather, compacting or pressing the mixture of scent reservoirs 11 and modulating coating 14 may be adjusted to achieve removal of excess modulating coating 14, to influence packing factor of the scent reservoirs 11, and to control the size of the voids 13 between the scent reservoirs 11. The mold (not shown) may, in some embodiments, be a wire mold or otherwise perforated to allow for air and excess modulating coating 14 to escape the mold during production of the aggregate article 10. Perforations of the mold also facilitate drying, as moisture and/or vapors may more easily escape the mold.

Once the mixture of scent reservoirs 11 and modulating coating 14 has been placed into a mold and compacted as necessary, the mold containing the mixture must be allowed to dry. Drying may be accomplished in ambient air. However, in certain embodiments, it may be preferable to dry the mixture using heat, ovens, heat tunnels, fans, or microwaves to speed the drying process. Once the mixture of scent reservoirs 11 and modulating coating 14 has dried, the aggregate article 10 may be removed from the mold. The combination of barrier substance 26 and hygroscopic substance 28 may comprise 1% to 20% of the total composition by weight of the dried modulating coating 14.

The aggregate article 10 may be adapted for use as a fragrance-release device in any number of applications. The geometry, sizing, materials, and type of volatile composition 24 used in the scent reservoirs 11 may be chosen specifically for an aggregate article 10, which is to be used in ambient air, on a table top, as a hanging fragrance-release device, or in combination with a heater or forced air assist. Similarly, the formulation, composition, and amount of modulating coating 14 used in the production of the aggregate article 10 may be adjusted or modified as required for any of the aforementioned uses.

The use of an aggregate article 10 made up of a plurality of scent reservoirs 11 may have additional functionality over the use of an article constructed from a single scent reservoir 11 or a similar number of loose, unbonded scent reservoirs 11, even when the same modulating coating 14 is applied. An aggregate article 10 comprising a plurality of scent reservoirs 11 that are bonded together using a modulating coating 14 may offer additional methods for regulating or controlling the release of the volatile composition 24 from the aggregate article 10. As described above, the modulating coating 14 may regulate the rate of release of the volatile composition 24 at high concentrations by slowing diffusion and also increasing the rate of diffusion when the concentration of volatile compositions 24 is lower (see FIG. 1 and associated description). However, an aggregate article 10 may introduce a second, geometry based regulation of the release of volatile compositions 24 from the aggregate article 10 and its associated scent reservoirs 11.

The aggregate article 10 compacts a plurality of scent reservoirs 11 into an aggregate mass. If the scent reservoirs 11 were left in as an agglomeration of loose, individual parts, the volatile compositions 24 held in the base material 12 of the scent reservoirs 11 would diffuse through the entire surface area of the scent reservoirs 11. However, when the scent reservoirs 11 are compacted into a matrix to create the aggregate article 10, a number of the scent reservoirs 11 will be positioned either partially or fully within the interior of the aggregate article 10. The compaction of the scent reservoirs 11 into an aggregate article 10 reduces the proportion of surface area to the volume of the scent reservoirs 11 and the amount of volatile compositions 24 held within the scent reservoirs 11.

Still referring to FIG. 2, the aggregate article 10 has a number of voids 13 between the compacted and bonded scent reservoirs 11. These voids 13 may be entirely closed to the ambient air, or they may be partially or fully exposed depending upon the location of the voids 13 and the arrangement of the scent reservoirs 11. In certain embodiments, a number of voids 13 may be linked or connected together such that a void 13 that is relatively far from the surface of the aggregate article 10 may have a passage for transfer of vapors and/or gases from the interior void 13 to the exterior surface of the aggregate article 10. This path, however, may be constricted, circuitous, or tortuous, slowing the exchange of gases or vapors from the inner portions of the aggregate article 10 to the surface. This constricted pathway for the volatile compositions 24 provides an additional mechanism for regulating or otherwise controlling the release of volatile compositions 24 into the surrounding environment.

Internal voids 13 in the aggregate article 10 may also control the release of volatile compositions 24 when they are closed off from the exterior surface of the aggregate article 10. Closed off internal voids 13, which do not have direct gas exchange with the external environment, will contain volatile compositions 24, which diffuse into the void 13 from the surrounding scent reservoirs 11. Initially, when the aggregate article 10 is new or relatively new, the scent reservoirs 11 will have approximately equal concentrations of volatile compositions 24. The diffusion from adjacent scent reservoirs 11 into the void 13 will be approximately equal and will continue until it reaches equilibrium. At this point, adjacent scent reservoirs 11 will absorb volatile compositions 24 from the void 13 at approximately the same rate as they release volatile compositions 24 into the void 13. At some point, the scent reservoirs 11 that are relatively closer to the surface of the aggregate article 10 will have lost a portion of their volatile compositions 24 to the surrounding environment. The scent reservoirs 11 that are relatively closer to the surface may share an internal void 13 with a scent reservoir 11 that is not directly exposed to the surface. The diffusion of volatile compositions 24 through the internal void 13 will become unbalanced, leading to a net transfer of volatile compositions 24 from a relatively more interior scent reservoir 11 to the relatively more exposed scent reservoir 11 through the internal void 13. This mechanism tends to delay the release of volatile compositions 24 from less exposed scent reservoirs 11 because the volatile compositions 24 must diffuse over a greater distance to the surface of the aggregate article 10 and must pass through multiple layers of the modulating coating 14. This multi-boundary control provides for longer lasting, more controlled release of volatile compositions 24 from the scent reservoirs 11.

Figure 9:
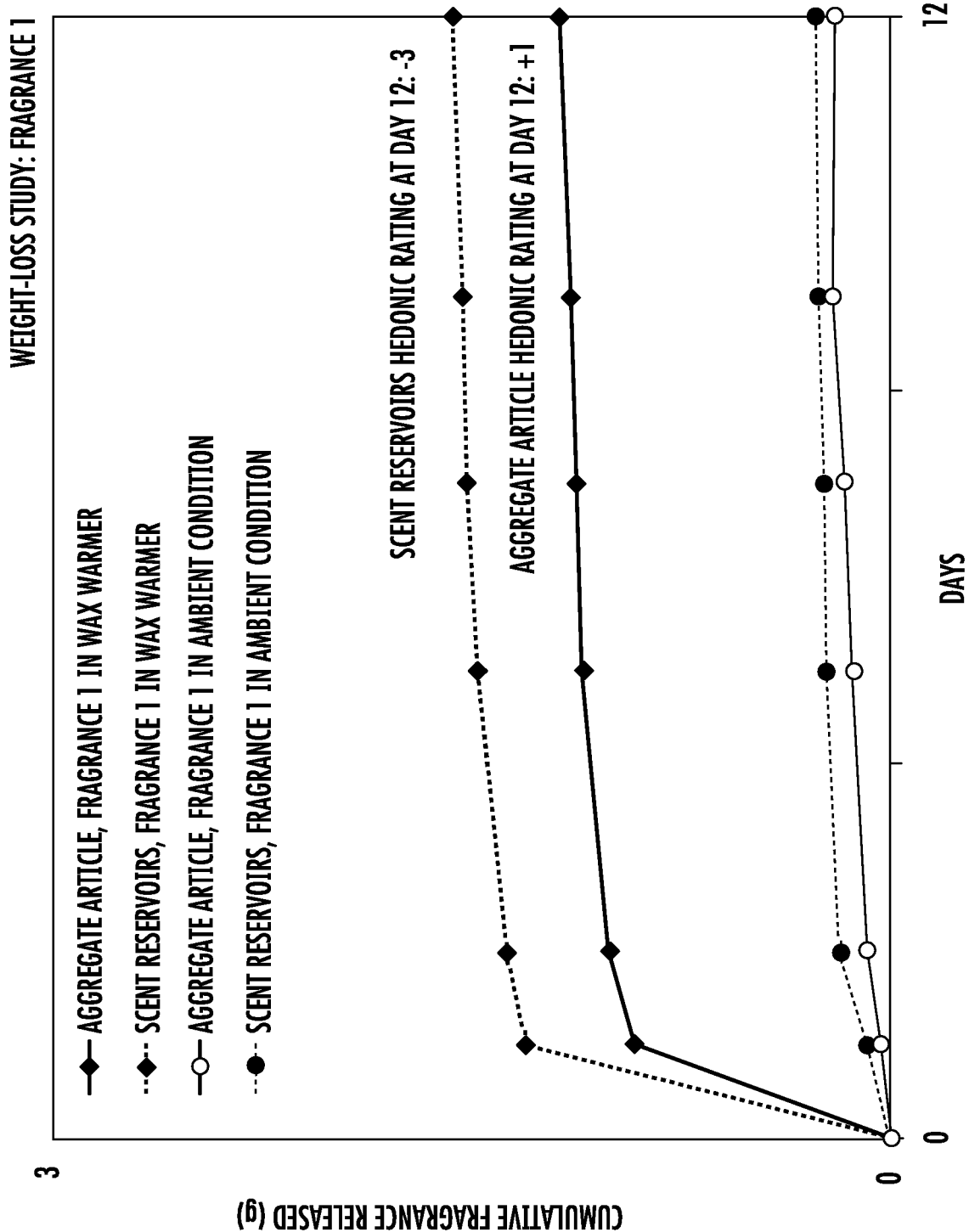
FIG. 9 is a graph showing a comparison of the cumulative amount released over time of a fragrance loaded in an aggregate fragrance-release device and loose scent reservoirs in both heated and ambient conditions.
Figure 10:
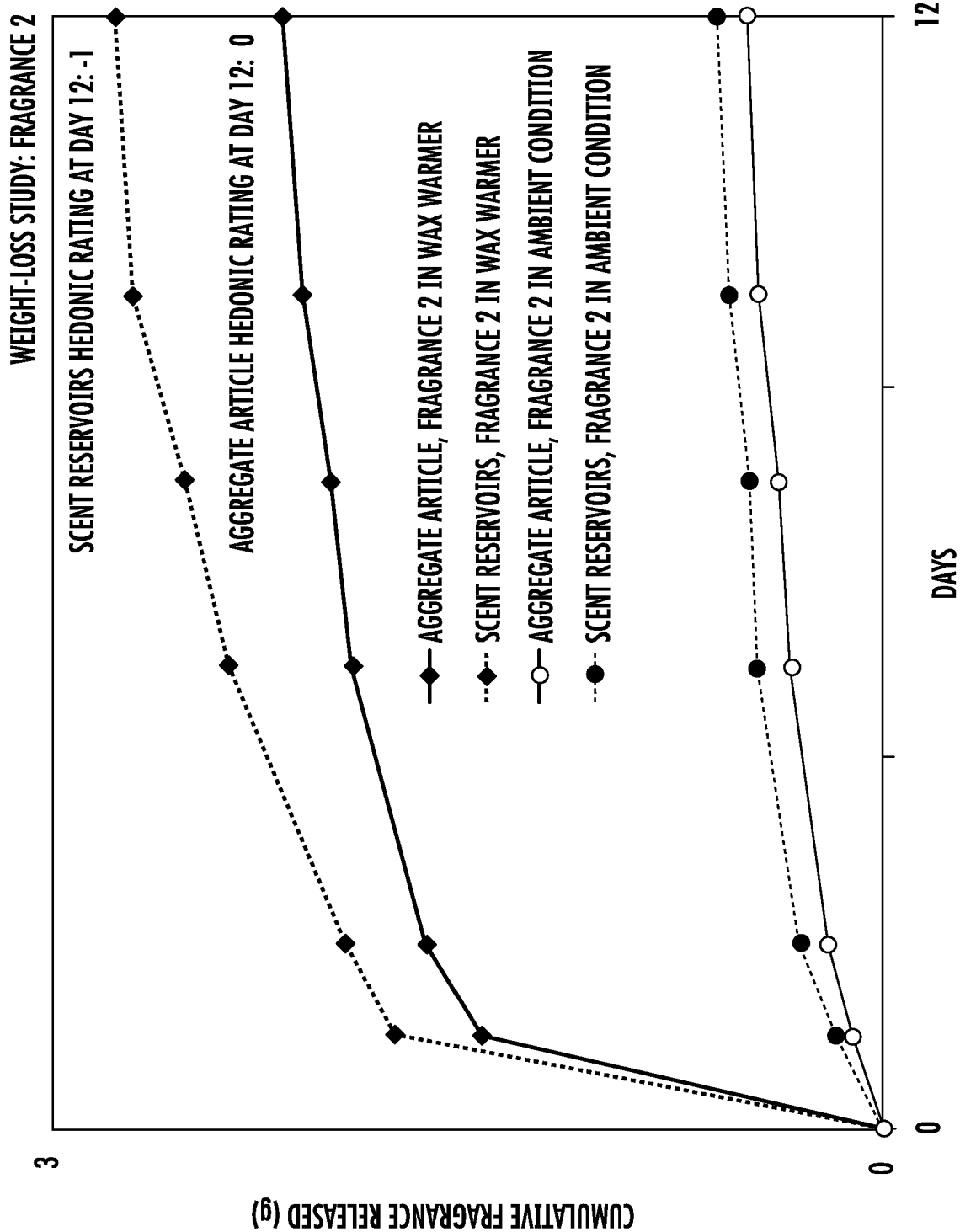
FIG. 10 is a graph showing a comparison of the hedonic impact and the cumulative amount released over time of a fragrance loaded in an aggregate fragrance-release device and loose scent reservoirs in both heated and ambient conditions.

FIGS. 9 and 10 are graphs that generally compare the cumulative release of a fragrance over time compared between loose scent reservoirs 11 and compacted or aggregate article 10, both in ambient and heated conditions. As shown, heated scent reservoirs 11 and aggregate articles 10 release a greater amount of fragrance than scent reservoirs 11 and aggregate articles 10 exposed to ambient conditions. However, under the same conditions, an aggregate article 10 releases fragrance more gradually than loose scent reservoirs 11. FIGS. 9 and 10 also provide hedonic ratings for the loose scent reservoirs 11 and a compacted or aggregate article 10 when heated. The hedonic rating is an indication of the impact of the scent released by the loose scent reservoirs 11 and aggregate article 10. The hedonic rating scale evaluates the scent on the following scale: −4 (extremely weak), −3 (very weak), −2 (moderately weak), −1 (slightly weak), 0 (just right), +1 (slightly strong), +2 (moderately strong), +3 (very strong), +4 (extremely strong). The general protocol for evaluating hedonic impact is as follows: (i) place test product in testing room (10' (w)×14' (1)×9' (h)) one hour before evaluation; (ii) direct panelists to enter the testing room and stand in a marked area approximately eight feet from test product; and (iii) instruct panelists to evaluate hedonic impact based on fragrance intensity.

Figure 6:
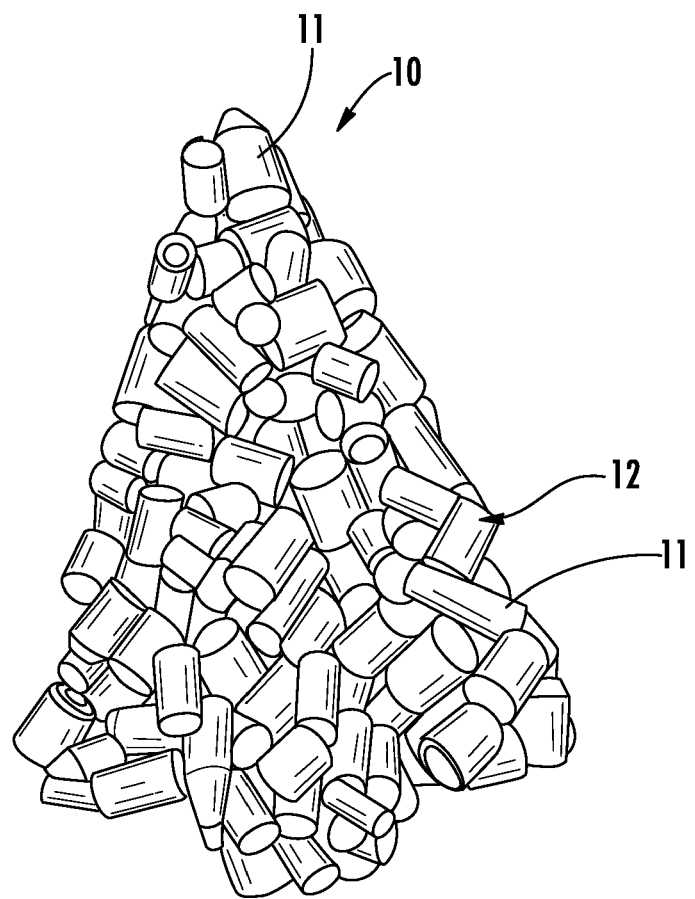
FIG. 6 is a perspective view of tree-shaped aggregate fragrance-release device.
Figure 7:
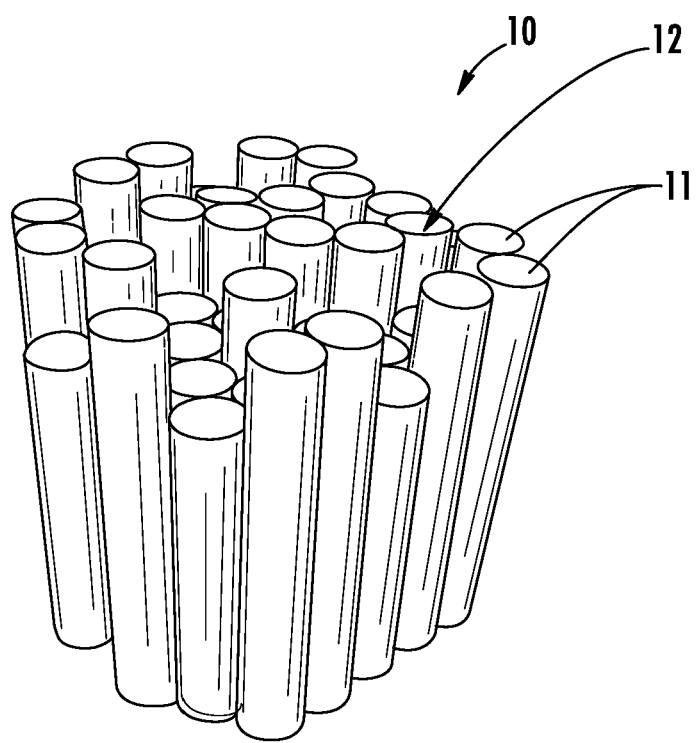
FIG. 7 is a perspective view of a columnar aggregate fragrance-release device.
Figure 8:
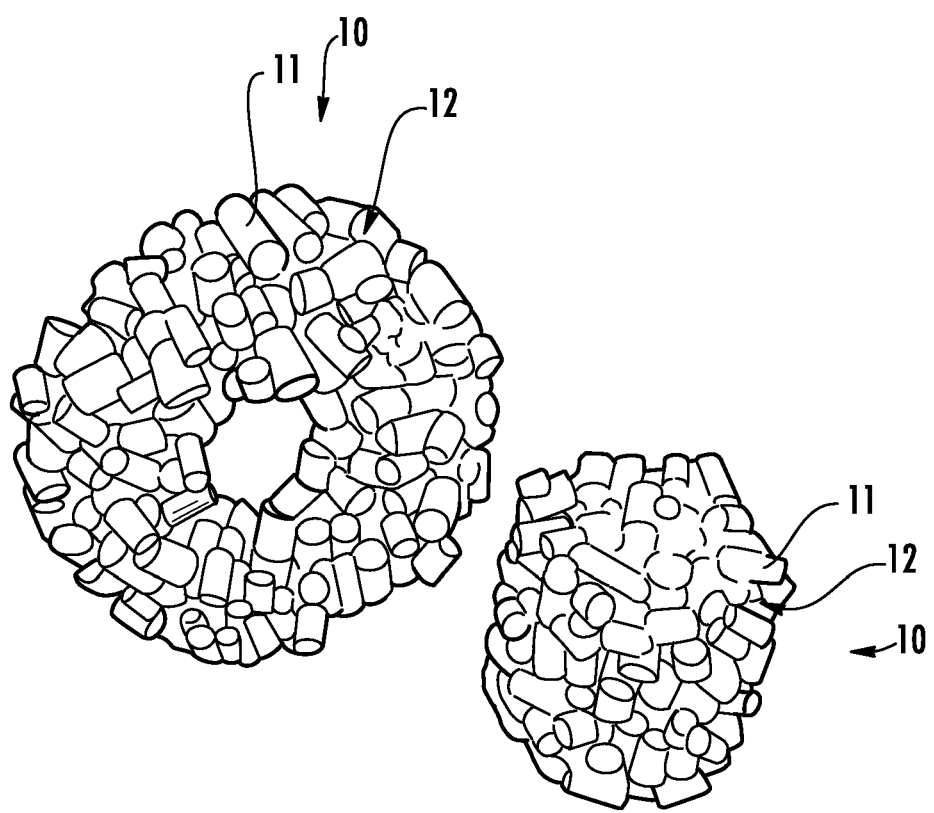
FIG. 8 is a perspective view of toroidal and cubic aggregate fragrance release devices.

FIGS. 3-8 are photographic depictions of different shapes of an aggregate article 10 comprising a plurality of scent reservoirs 11. Each scent reservoir 11 may be comprised of a base material 12, which is infused with volatile compositions 24 (not shown) and coated with a moderating coating 14 (not shown). Any number of shapes may be made using the previously-described manufacturing method. Some exemplary, non-limiting shapes are shown in FIGS. 3-8, including spherical (FIG. 3), pyramidal (FIG. 4), heart-shaped (FIG. 5), tree-shaped (FIG. 6), a stick pile (FIG. 7), toroidal, and cubic (FIG. 8). Additional variations in shape, size, and level of compaction are possible. In certain embodiments, as shown in FIG. 6, the scent reservoirs 11 and resulting aggregate article 10 may be dyed or otherwise pigmented to produce any desired color of the final product. Also, in some embodiments, as shown in FIG. 7, the scent reservoirs 11 may be relatively larger or smaller. In FIG. 7, the scent reservoirs 11 are large enough that they may be sold individually as fragrance-release devices, or they may be used as constituents in an aggregate article 10.

The different shapes of the aggregate articles 10 shown in FIGS. 3-8 may serve to provide an aesthetically pleasing aggregate article 10. However, differing shapes of the aggregate article 10 also provide for different function of the aggregate article 10 and provide another means of controlling the release of volatile compositions 24 from the scent reservoirs 11 of the aggregate article 10. Adjustments or alterations to the overall shape of the aggregate article 10 may influence the rate of release of the volatile compositions 24 in a number of ways. For example, changes to the shape of the aggregate article 10 may influence the ratio of surface area to volume or the ratio of exposed scent reservoirs 11 to interior scent reservoirs 11. The shape of the aggregate article 10 may also affect the interaction of the aggregate article 10 with other devices, such as fans, forced air blowers, or heaters. For example, the efficiency of a fan or forced air blower on the aggregate article 10 will increase or decrease depending on whether the shape of the aggregate article 10 encourages efficient contact between the surfaces of the scent reservoirs 11 and the air current. In certain embodiments, the aggregate article 10 may be used in combination with a heater to warm the aggregate article 10 and its constituent scent reservoirs 11. The shape of the aggregate article 10 will determine the amount of contact area between the heater and the aggregate article 10, and also the average distance of the scent reservoirs 11 from the heat source, regardless of whether or not they are in direct contact.

FIG. 11 is a graph showing a comparison of cumulative fragrance release for differently shaped aggregate articles 10 and loose scent reservoirs 11. As shown, a short and wide aggregate article 10 releases its volatile compositions 24 more quickly than a medium or tall and thin aggregate article 10. The short and wide aggregate article 10 only slightly outperforms the loose scent reservoirs 11 over time in a heated condition. One reason for this difference in performance may be that the short and wide aggregate article 10 has a greater area of contact with the heater, giving a higher level of heat transfer. Furthermore, the individual scent reservoirs 11 are, on average, closer to the heat source. By contrast, the tall, thin aggregate article 10 may have a smaller contact area with the heat source, and the average distance of the scent reservoirs 11 is greater. The result is that fewer scent reservoirs 11 are at a higher temperature and will more release the volatile compositions 24 at a slower rate.

As discussed above, an aggregate article 10 that is to be used with a heat source should comprise a modulating coating 14, which is formulated to tolerate temperatures that the aggregate article 10 is likely to encounter with a heating device, such as a wax warmer. The modulating coating 14 must have enough heat tolerance to not only maintain function as a moderator of the release of volatile compositions 24, but it must also maintain its bonding properties at elevated temperatures to prevent disintegration of the aggregate article 10 and its matrix of scent reservoirs 11. Unintended changes to the shape of the aggregate article 10 may lead to uncontrolled release of the volatile compositions 24 and a potential deterioration of performance.

The modulating coating 14 may be applied to the base material 12 before or after application of the volatile composition 24. For example, the modulating coating 14 may be applied when the base material 12 is in a two-dimensional form via conventional two-dimensional coating methods typically used for treating two-dimensional sheets of material, such as paper. These methods include but are not limited to at least one of gravure printing, offset printing, flexographic printing, rod coating, blade coating, curtain coating, or other suitable coating methods. In these two-dimensional embodiments, the modulating coating 14 may be applied to the base material 12 when the base material 12 is in a single two-dimensional layer, after which the base material 12 layers are assembled together to form the article 10. In other two-dimensional embodiments, the base material 12 may be arranged into the layered material prior to application of the modulating coating 14 so that the modulating coating 14 is only applied to the outermost surface 16 of the top layer of the base material 12 (although the modulating coating 14 may penetrate to a certain depth within the article 10).

In other embodiments, the modulating coating 14 may be applied to the mold containing scent reservoirs 11 that will become the three-dimensional article 10 via an infusion method with the add-on infusion ranging from 1% to 20% by dry weight, and, in certain embodiments, may further range from 1% to 10% by dry weight.

In certain embodiments, the modulating coating 14 may be applied to the base material 12 or scent reservoirs 11 via pouring and mixing. In yet other embodiments, the modulating coating 14 may be applied to the base material 12 or scent reservoirs 11 via spray treatment.

The volatile composition 24 may be applied to the base material 12 before or after application of the modulating coating 14, as described above. For example, the volatile composition 24 may be applied by placing the base material 12 and/or the scent reservoirs 11 in intimate contact with the volatile composition 24 for a period of time. The volatile composition 24 may be in any physical state, such as liquid, solid, gel, or gas. For convenience, a liquid volatile composition 24 is described, but this is not intended to be limiting. The interaction time may depend on the concentration or type of volatile composition 24 being applied to the base material 12 and/or the scent reservoirs 11, and/or how strong or intense of a volatile composition 24 release desired, and/or the type of base material 12. In certain embodiments, the scent reservoirs 11 may be infused with a liquid fragrance composition. The amount of liquid fragrance composition and the saturation time for infusing the scent reservoirs 11 and/or aggregate article 10 with the liquid fragrance composition will vary depending on the particular parameters of the application. For example, the size of the scent reservoirs 11, the size of the aggregate article 10, the characteristics of the liquid fragrance (e.g. viscosity, concentration, compatibility with the material of the scent reservoirs 11 and/or aggregate article 10, and strength of scent), the holding capacity of the scent reservoirs 11 and/or aggregate article 10, and the expected service life of the scent reservoirs 11 and/or aggregate article 10 will influence the amount of liquid fragrance composition infused and the necessary saturation time. The base material 12 and/or scent reservoirs 11 may be pre-treated prior to exposure to the volatile composition 24. For example, the base material 12 and/or scent reservoirs 11 may be placed in a drying oven to remove any residual moisture. Further method steps comprise pressure treating and/or vacuum treating the base material 12 and/or scent reservoirs 11. After treatment, the base material 12 and/or scent reservoirs 11 may be dried, for example by rubbing or patting dry, and/or by other methods known for drying a surface, and/or may be left to air dry. Drying steps may be used before or after other steps described herein.

In some embodiments, a method for applying the volatile composition 24 to the base material 12 and/or scent reservoirs 11 comprises combining the volatile composition 24 and the base material 12 and/or scent reservoirs 11 in a container and applying a pressure above atmospheric pressure on the volatile composition 24 and base material 12 and/or scent reservoirs 11. Pressure may be applied in a range from about 1 psi to about 40 psi, from about 5 psi to about 30 psi, or from about 10 psi to about 20 psi, at about 5 psi, at about 10 psi, at about 15 psi, at about 20 psi, at about 25 psi, at about 30 psi, at about 35 psi, at about 40 psi, and/or at pressures therein between. The pressure may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or scent reservoirs 11 to achieve a desired load of the volatile composition 24 to the base material 12 and/or scent reservoirs 11 or release of the volatile composition 24 from the base material 12 and/or scent reservoirs 11. Appropriate pressures and times for a particular embodiment can be determined by one skilled in the art based on the identities and characteristics of the particular volatile composition 24 and base material 12 and/or scent reservoirs 11.

In certain embodiments, a method for applying the volatile composition 24 comprises combining the volatile composition 24 and base material 12 and/or scent reservoirs 11 in a container and applying a vacuum below atmospheric pressure to the volatile composition 24 and the base material 12 and/or scent reservoirs 11. Vacuum may be applied in a range from 0.001 mm Hg to about 700 mm Hg, or from about 5 Kpa to about 35 kPa, from about 10 Kpa to about 25 kPa, from about 20 Kpa to about 30 kPa, from about 15 Kpa to about 25 kPa, from about 25 Kpa to about 30 kPa, at about 5 kPa, at about 6 kPa, at about 7 kPa, at about 8 kPa, at about 9 kPa, at about 10 kPa, at about 15 kPa, at about 16 kPa, at about 17 kPa, at about 18 kPa, at about 19 kPa, at about 20 kPa, at about 22 kPa, at about 24 kPa, at about 26 kPa, at about 28 kPa, at about 30 kPa, and vacuums therein between. The vacuum may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or scent reservoirs 11 to achieve a desired load of the volatile composition 24 to the base material 12 and/or scent reservoirs 11 or release of the volatile composition 24 from the base material 12 and/or scent reservoirs 11.

In yet other embodiments, the method may comprise pressure and vacuum steps. The volatile composition 24 and the base material 12 and/or scent reservoirs 11 may be combined and undergo vacuum treatment and pressure treatment, in no particular order. For example, the volatile composition 24 and the base material 12 and/or scent reservoirs 11 may be combined in a container in an air-tight apparatus and a vacuum of 20 mm Hg to 80 mm Hg may be applied for about 1 minute to 10 hours. Pressure treatment of 1 psi to 40 psi may be applied for about 1 minute to about 10 hours and the time and amount of vacuum or pressure treatment may vary and depend upon the amount of volatile composition 24 to be loaded in the base material 12 and/or scent reservoirs 11, the type of base material 12 used, the intended use of the scent reservoirs 11, and other characteristics of the scent reservoirs 11.

In certain embodiments, the base material 12 and/or scent reservoirs 11 may be pre-treated with colorants, followed by treatment with the modulating coating 14. Colorants may include natural and synthetic dyes, water-resistant dyes, oil-resistant dyes, and combinations of water- and oil-resistant dyes. Colorants may be selected based on the composition of the base material 12 or scent reservoirs 11, and is well within the skill of those in the art. Suitable water-resistant colorants include oil soluble colorants and wax soluble colorants. Examples of oil soluble colorants include Pylakrome Dark Green and Pylakrome Red (Pylam Products Company, Tempe Ariz.). Suitable oil-resistant colorants include water soluble colorants. Examples of water soluble colorants include FD&C Blue No. 1 and Carmine (Sensient, St. Louis, Mo.). A Lake type dye may also be used. Examples of Lake dyes are Cartasol Blue KRL-NA LIQ and Cartasol Yellow KGL LIQ (Clariant Corporation, Charlotte, N.C.). Pigments may also be used in coloring the base material 12 and may be added during or after the manufacture of the base material 12 and/or scent reservoirs 11. Such coloring or dying methods are known to those skilled in the art, and any suitable dyes, pigments, or colorants are contemplated by the present invention. Colorants may be used to affect the overall surface charge of the silica or other hygroscopic substance 28 to enhance the interaction with the coating.

EXAMPLES

Example 1. Synthesis of the Adhesive/Modulating Coating for 3D Aggregate Article Manufacture The composition for the adhesive/modulating coating 14 is made by mixing two components, a modified starch and a silica suspension. One example of a modified starch is liquid starch (P30L) from Grain Processing (Muscatine, Iowa). Other liquid starches, pre-gelled starches, or dry modified starches can be used with the proper make-down and/or cooking equipment. One example of a silica suspension is Snowtex®-O from Nissan Chemical America Corporation (Houston, Tex.). Other silica suspensions may also be adequate. The adhesive/modulating coating mixture is made by thoroughly mixing P30L with Snowtex®-O in the ratio 55% P30L and 45% Snowtex®-O (wt/wt). This ratio is adjustable depending on the needed adhesive strength for the shape being made.

Example 2. Manufacture of 3D Aggregate Article

Aggregate article 10 is made by gluing enough loose scent reservoirs 11 to form the desired shape and size; the glue used is the adhesive/modulating coating 14 described in Example 1. One example of a loose scent reservoir 11 is a paper media comprised of cut ends from spiral wound paper stick manufacturing. Other absorbent material in small piece form may also be used. Scent reservoirs 11 may be pre-dyed to the desired color. The shape of the aggregate article 10 is enabled by a mold, which may consist of a wire mold or other constraining device that allows the scent reservoirs 11 to be formed into the desired shape. Molds with a multitude of openings (smaller than the size of the scent reservoirs 11) are preferred, since they allow for more efficient drying. Drying methods may include the use of ovens, heat tunnels, fan, ambient air, microwaves, etc. The manufacture process starts with mixing the loose scent reservoirs 11 with the adhesive/modulating coating 14 mixture at a ratio of 75% to 25% (wt/wt). The ratio may be adjusted to meet the desired property; and this ratio range may be 10% to 90% (wt/wt) and 90% to 10% (wt/wt). The mixture of loose scent reservoirs 11 and adhesive/modulating coating 14 is placed in a mold and press in place firmly to fill any voids in the mold (except for the voids between scent reservoirs 11 based on geometry). The filled-mold in an oven/heat tunnel for accelerated drying, or allowed to dry at ambient conditions or under a fan overnight. Once dried, the formed aggregate article 10 is popped out of the mold. Adding fragrance to the aggregate article 10 may be done by (i) carefully adding a specified amount (15% (wt/wt) in one embodiment) to the aggregate article 10 with a dropper, (ii) quickly dipping the aggregate article 10 into the fragrance, (iii) running the aggregate article 10 through a fragrance curtain (similar to curtain coating), (iv) completely infusing the aggregate article 10 in fragrance under vacuum or (v) any other suitable method. The amount of fragrance loaded can be varied to achieve the appropriate hedonic effect for the size and shape of aggregate article 10.

Example 3. Weight-Loss Study to Evaluate Fragrance Release

The rate and duration of fragrance release by a aggregate article 10 (and other product formats) on a commercial wax warmer were evaluated by measuring the weight-loss over time. Commercially available wax warmers were purchased and used without modification. The aggregate article 10 containing fragrance is placed in the wax warmer holder; and the mass of the holder and aggregate article 10 with fragrance is recorded. The test sample containing holder is placed on the wax warmer, and the wax warmer is turned on. At specified time, the mass of the holder with test sample is recorded. In parallel, the hedonic impact of the fragrance released is evaluated at a specified time by a simple rating scale by a human subject. The rating scale is: −4 (extremely weak), −3 (very weak), −2 (moderately weak), −1 (slightly weak), 0 (just right), +1 (slightly strong), +2 (moderately strong), +3 (very strong), +4 (extremely strong).

FIG. 9 is a plot showing cumulative release of Fragrance 1 over time. The results show the aggregate article 10 format in wax warmer has a better fragrance release profile and hedonic impact than the loose scent reservoirs 11 format in wax warmer. The implication is an even, longer duration of fragrance release for the aggregate article 10.

FIG. 10 is a plot showing cumulative release of Fragrance 2 over time. The results show the aggregate article 10 format in wax warmer has a better fragrance release profile and hedonic impact than the loose scent reservoirs 11 format in wax warmer. The implication is an even, longer duration of fragrance release for the aggregate article 10.

FIG. 11 is a plot showing cumulative release of Fragrance 2 over time. The results show the impact of aggregate article 10 shape and size on fragrance release. Increasing size, specifically increasing contact area to the heated surface of a wax warmer allows for more fragrance release. Increasing distance (height of aggregate article 10) from the heated surface of a wax warmer decreases the initial fragrance release, but this allows for increased duration of fragrance release.

Each of the above noted test runs was undertaken using identical fragrances, amounts of fragrance, scent reservoirs 11 (whether in loose or aggregate article 10 format), and applications of heat. The loose scent reservoirs 11 and aggregate articles 10 used their respective appropriate formulations and mixtures of the modulating coating 14 as necessary to achieve the required bonding characteristics for testing.

That which is claimed is:

1. An aggregate article comprising:
a plurality of scent reservoirs comprising an absorbent matrix material, the plurality of scent reservoirs constructed into a three-dimensional matrix via a modulating coating bonding between the plurality of scent reservoirs;
a volatile composition, wherein at least some of the volatile composition is located in the absorbent matrix material;
wherein the modulating coating at least partially covers each of the plurality of scent reservoirs and comprises a barrier substance and hygroscopic silica having a diameter ranging from 1 nm to 100 nm;
wherein the barrier substance hinders a release of the volatile composition through the modulating coating; and
wherein the hygroscopic silica facilitates the release of the volatile composition through the modulating coating.

2. The aggregate article of claim 1, wherein the barrier substance comprises a starch.

3. The aggregate article of claim 1, wherein the modulating coating is configured to resist temperatures higher than ambient and to resist direct heating.

4. The aggregate article of claim 3, wherein a weight ratio of the barrier substance to the hygroscopic silica is at least one of approximately 75:25 and approximately 25:75.

5. The aggregate article of claim 3, wherein the modulating coating comprises approximately 45 to 60 percent barrier substance by weight.

6. The aggregate article of claim 3, wherein the modulating coating comprises approximately 40 to 55 percent hygroscopic substance by weight.

7. The aggregate article of claim 3, wherein a weight ratio of the barrier substance to the hygroscopic silica is approximately 55:45.

8. The aggregate article of claim 1, wherein:
the plurality of scent reservoirs comprises at least one scent reservoir selected from the group consisting of wound paper, extruded pulp, wood chips, fiber bundles, and ceramic chunks;
at least some of the volatile composition is located within the modulating coating; and
the modulating coating further comprises water that is absorbed or adsorbed to the hygroscopic silica.

9. An aggregate article comprising:
a plurality of scent reservoirs comprising an absorbent matrix comprising pores;
a volatile composition, wherein at least some of the volatile composition is located in the pores;
a modulating coating distributed on at least a portion of exterior surfaces of the plurality of scent reservoirs and comprising a barrier substance and hygroscopic silica having a diameter ranging from 1 nm to 100 nm;
wherein the modulating coating is formulated to provide a heat resistant bond between the plurality of scent reservoirs; and
wherein the modulating coating regulates a release rate of the volatile composition located in the pores.

10. The aggregate article of claim 9, wherein the barrier substance comprises a starch.

11. The aggregate article of claim 9, wherein the modulating coating is configured to resist temperatures higher than ambient and to resist direct heating.

12. The aggregate article of claim 11, wherein a weight ratio of the barrier substance to the hygroscopic silica is at least one of approximately 75:25 and approximately 25:75.

13. The aggregate article of claim 11, wherein the modulating coating comprises approximately 45 to 60 percent barrier substance by weight.

14. The aggregate article of claim 11, wherein the modulating coating comprises approximately 40 to 55 percent hygroscopic substance by weight.

15. The aggregate article of claim 11, wherein a weight ratio of the barrier substance to the hygroscopic silica is approximately 55:45.

16. The aggregate article of claim 9, wherein:
the plurality of scent reservoirs comprises at least one scent reservoir selected from the group consisting of wound paper, extruded pulp, wood chips, fiber bundles, and ceramic chunks;
at least some of the volatile composition is located within the modulating coating; and
the modulating coating further comprises water that is absorbed or adsorbed to the hygroscopic silica.

17. An aggregate article comprising:
a plurality of scent reservoirs comprising an absorbent matrix material, the plurality of scent reservoirs constructed into a three-dimensional matrix via a modulating coating bonding between the plurality of scent reservoirs;
a volatile composition, wherein at least some of the volatile composition is located in the absorbent matrix material;
wherein the modulating coating at least partially covers an exterior surface of each of the plurality of scent reservoirs and comprises a barrier substance and hygroscopic silica having a diameter ranging from 1 nm to 100 nm;
wherein the barrier substance hinders a release of the volatile composition through the modulating coating; and
wherein the hygroscopic silica facilitates the release of the volatile composition through the modulating coating.

18. The aggregate article of claim 17, wherein the barrier substance comprises a starch.

19. The aggregate article of claim 17, wherein the modulating coating is configured to resist temperatures higher than ambient and to resist direct heating.

20. The aggregate article of claim 17, wherein:
the plurality of scent reservoirs comprises at least one scent reservoir selected from the group consisting of wound paper, extruded pulp, wood chips, fiber bundles, and ceramic chunks;
at least some of the volatile composition is located within the modulating coating; and
the modulating coating further comprises water that is absorbed or adsorbed to the hygroscopic silica.

* * * * *